(12) United States Patent
Gallop et al.

(10) Patent No.: US 7,420,002 B2
(45) Date of Patent: *Sep. 2, 2008

(54) AMINO ACID CONJUGATES PROVIDING FOR SUSTAINED SYSTEMIC CONCENTRATIONS OF GABA ANALOGUES

(75) Inventors: Mark Gallop, Los Altos, CA (US); Kenneth C. Cundy, Redwood City, CA (US); Randall A. Scheuerman, Santa Clara, CA (US); Ronald W. Barrett, Saratoga, CA (US); Noa Zerangue, San Carlos, CA (US)

(73) Assignee: Xenoport, Santa Clara, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/480,293

(22) PCT Filed: Jun. 11, 2002

(86) PCT No.: PCT/US02/18493

§ 371 (c)(1),
(2), (4) Date: Jul. 13, 2004

(87) PCT Pub. No.: WO02/100344

PCT Pub. Date: Dec. 19, 2002

(65) Prior Publication Data

US 2004/0254344 A1 Dec. 16, 2004

Related U.S. Application Data

(60) Provisional application No. 60/364,619, filed on Mar. 18, 2002, provisional application No. 60/297,732, filed on Jun. 11, 2001.

(51) Int. Cl.
*A61K 31/195* (2006.01)
*C07C 229/28* (2006.01)

(52) U.S. Cl. .................... 514/564; 562/561; 549/13; 549/426; 514/432; 514/459

(58) Field of Classification Search .............. 514/564, 514/438, 365, 357, 311, 432, 459; 562/561; 546/152, 153, 335; 548/204; 549/58, 76, 549/13, 426

See application file for complete search history.

(56) References Cited

U.S. PATENT DOCUMENTS

| | | |
|---|---|---|
| 2,996,431 A | 8/1961 | Barry |
| 3,139,383 A | 6/1964 | Neville et al. |
| 3,402,240 A | 9/1968 | Cain et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,024,175 A | 5/1977 | Satzinger et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,087,544 A | 5/1978 | Satzinger et al. |
| 4,088,864 A | 5/1978 | Theeuwes et al. |
| 4,093,709 A | 6/1978 | Choi et al. |
| 4,200,098 A | 4/1980 | Ayer et al. |
| 4,285,987 A | 8/1981 | Ayer et al. |
| 4,421,736 A | 12/1983 | Walters et al. |
| 4,434,153 A | 2/1984 | Urquhart et al. |
| 4,508,728 A | 4/1985 | Nagai et al. |
| 4,721,613 A | 1/1988 | Urquhart et al. |
| 4,752,470 A | 6/1988 | Mehta |
| 4,816,263 A | 3/1989 | Ayer et al. |
| 4,820,523 A | 4/1989 | Shtohryn et al. |
| 4,853,229 A | 8/1989 | Theeuwes |
| 4,908,353 A | 3/1990 | Yamamoto et al. |
| 5,084,479 A | 1/1992 | Woodruff |
| 5,094,848 A | 3/1992 | Brixner |
| 5,110,797 A | 5/1992 | Ienaga et al. |
| 5,563,175 A | 10/1996 | Silverman et al. |
| 6,001,876 A | 12/1999 | Singh |
| 6,020,370 A | 2/2000 | Horwell et al. |
| 6,028,214 A | 2/2000 | Silverman et al. |
| 6,051,683 A | 4/2000 | Deigin et al. |
| 6,103,932 A | 8/2000 | Horwell |
| 6,117,906 A | 9/2000 | Silverman et al. |
| 6,140,366 A | 10/2000 | Silverman et al. |
| 6,171,615 B1 | 1/2001 | Roussin et al. |
| 6,255,345 B1 | 7/2001 | Silverman et al. |
| 6,291,526 B1 | 9/2001 | Silverman et al. |
| 6,342,529 B1 | 1/2002 | Silverman et al. |
| 6,375,987 B1 | 4/2002 | Farah et al. |
| 6,379,700 B2 | 4/2002 | Joachim et al. |
| 6,833,140 B2 * | 12/2004 | Cundy et al. ............. 424/468 |

FOREIGN PATENT DOCUMENTS

| | | |
|---|---|---|
| EP | 1 178 034 | 2/2002 |
| GB | 2362646 | 11/2001 |
| SU | 285929 | 1/1971 |
| WO | WO 92/09560 | 6/1992 |

(Continued)

OTHER PUBLICATIONS

Adibi, SA, "The Oligopeptide Transporter in Human Intestine: Biology and Function", *Gastroenterology*, 1997, vol. 113, pp. 332-340.

(Continued)

*Primary Examiner*—Charanjit S Aulakh
(74) *Attorney, Agent, or Firm*—Buchanan Ingersoll & Rooney, P.C.

(57) ABSTRACT

Compounds that provide for sustained systemic concentrations of GABA analogs following oral administration to animals are disclosed. Pharmaceutical compositions including, and methods using, such compounds are also disclosed.

11 Claims, 3 Drawing Sheets

FOREIGN PATENT DOCUMENTS

| | | |
|---|---|---|
| WO | WO 93/23383 | 11/1993 |
| WO | WO 97/29101 | 8/1997 |
| WO | WO 97/33858 | 9/1997 |
| WO | WO 97/33859 | 9/1997 |
| WO | WO 98/17627 | 4/1998 |
| WO | WO 99/08671 | 2/1999 |
| WO | WO 99/21824 | 5/1999 |
| WO | WO 99/31057 | 6/1999 |
| WO | WO 99/31074 | 6/1999 |
| WO | WO 99/31075 | 6/1999 |
| WO | WO 99/37296 | 7/1999 |
| WO | WO 99/61424 | 12/1999 |
| WO | WO 00/15611 | 3/2000 |
| WO | WO 00/23067 | 4/2000 |
| WO | WO 00/31020 | 6/2000 |
| WO | WO 00/50027 | 8/2000 |
| WO | WO 01/20331 | 3/2001 |
| WO | WO 01/90052 | 11/2001 |
| WO | WO 02/00209 | 1/2002 |
| WO | WO 02/28411 | 4/2002 |
| WO | WO 02/28881 | 4/2002 |
| WO | WO 02/28882 | 4/2002 |
| WO | WO 02/28883 | 4/2002 |
| WO | WO 02/32376 | 4/2002 |
| WO | WO 02/42414 | 5/2002 |

OTHER PUBLICATIONS

Alderman, "A Review of Cellulose Ethers in Hydrophilic Matrices for Oral Controlled-Release Dosage Forms", *Int. J. Pharm. Tech. & Prod. Mfr.*, 1984, vol. 5, No. 3, pp. 1-9.
Bamba et al., "Release Mechanisms in Gelforming Sustained Release Preparations", *Int. J. Pharm.*, 1979, vol. 2, p. 307.
Bryans et al., "3-substituted GABA Analogs with Central Nervous System Activity: A Review", *Med. Res. Rev.*, 1999, vol. 19, pp. 149-177.
Coleman et al., "A Practical Guide to Polymer Miscibility", *Polymers*, 1990, vol. 31, pp. 1187-1231.
Dieck, ST et al., "The Peptide Transporter PepT2 is Expressed in Rate Brain and Mediates the Accumulation on the Fluorescent Dipeptide Derivative μ-Ala-Lys-Nε-AMCA in Astrocytes", *GLIA*, 1999, vol. 25, pp. 10-20.
During et al., "Controlled Release of Dopamine From a Polymeric Brain Implant: In Vivo Characterization" *Ann. Neurol.*, 1989, vol. 25, p. 351.
Fincher, "Particle Size of Drugs and Its Relationship to Absorption and Activity", *J. Pharm. Sci.*, 1968, vol. 57, pp. 1825-1835.
Gidal et al., "Inter- and Intra-Subject Variability in Gabapentin Absorption and Absolute Bioavailability", *Epilepsy Res.*, 2000, vol. 40, pp. 123-127.
Gidal et al., "Gabapentin Bioavailability: Effect of Dose and Frequency of Administration in Adult Patients with Epilepsy", *Epilepsy Res.*, 1998, vol. 31, pp. 91-99.
Goodson, "Dental Applications", *Medical Applications of Controlled Release*, 1984, vol. 2, Ch. 6, pp. 115-138.
Hoes, CJT, et al., "The Application of Drug-Polymer Conjugates in Chemotheraphy", *Drug Carrier Systems*, 1989, vol. 9, pp. 57-60.
Howard et al., "Intracebral Drug Delivery in Rats With Lesion-Induced Memory Deficits":, *J. Neurosurg.*, 1989, vol. 71, p. 105.
Jezyk et al., "Transport of Pregabalin in Rat Intestine and Caco-2 Monolayers", *Pharm. Res.*, 1999, vol. 16, pp. 519-526.
Langer, "New Methods of Drug Delivery", *Science*, 1990, vol. 249, pp. 1527-1533.
Langer and Peppas, "Chemical and Physical Structure of Polymers as Carriers of Controlled Release of bioactive Agents: A Review", *JMS-Rev. Macromol. Chem. Phys.*, 1983, vol. 23, p. 61-126.
Leibach et al., "Peptide Transporters in the Intestine and the Kidney", *Ann. Rev. Nutr.*, 1996, vol. 16, pp. 99-119.
Leong et al., "Polymeric Controlled Drug Delivery", *Adv. Drug Delivery Rev.*, 1987, vol. 1, pp. 199-233.
Levy et al., "Inhibition of Calcification of Bioprosthetic Heart Valves by Local Controlled-Release Diphosphonate", *Science*, 1985, vol. 228, p. 190.
Linhardt, R. "Biodegradable Polymers", *Controlled Release of Drugs*, 1989, Chp. 2, pp. 53-95.
Lu, "Dimensionless Presentation for Drug Release From a Coated Pure Drug Bead", *Int. J. Pharm.*, 1994, vol. 112, pp. 117-124.
Magnus, "Nonepileptic Uses of Gabapentin", *Epilepsia*, 1999, vol. 40, pp. S66-S72.
Navia and Charurvedi, "Design Principles for Orally Bioavailable Drugs", *Drug Discovery Today*, 1996, vol. 1, pp. 179-189.
Radulovic et al., "Disposition of Gabapentin in Mice, Rats, Dogs and Monkeys", *Drug Metab. Dispos.*, 1995, vol. 23, pp. 441-448.
Remington (editor). *Pharmaceutical Sciences*, 1970, $14^{th}$ ed. pp. 1626-1628.
Remington (editor), *Pharmaceutical Sciences*, 1985, $17^{th}$ ed., Ch. 90, pp. 1603-1625.
Seudek et al., "A Preliminary Trial of the Programmable Implantable Medication System for Insulin Delivery", *New England J. of Med.*, 1989, vol. 321, p. 574.
Sefton, "Implantable Pumps", *CRC Crit. Ref. Biomed. Eng.*, vol. 14, p. 201.
Tsuji et al., "Carrier-Mediated Intestinal Transport of Drugs", *Pharm. Res.*, 1996, vol. 13, pp. 963-977.
Verma et al., "Osomotically Controlled Drug Delivery", *Drug Dev. Ind. Pharm.*, 2000, vol. 26, pp. 695-708.
Wang et al., "Electrophysiological Characteristics of the Proton-Coupled Peptide Transporter PEPT2 Cloned from Rat Brian", *Am. J. Physiol.*, 1998, vol. 275, pp. C967-C975.
Sugawara Mitsuru et al., "Transport of Valganciclovir, a Ganciclovir Prodrug, via Peptide Transporters PEPT1 and PEPT2", Journal of Pharmaceutical Sciences, vol. 89, No. 6, Jun. 2000, pp. 781-789, XP001182733.
Praveen V. Balimane et al., "Direct Evidence of Peptide Transporter (Pept1)-Mediated Uptake of a Nonpeptide Prodrug, Valacyclovir", Biochemical and Biophysical Research Communications, vol. 250, No. 2, Sep. 18, 1998, pp. 246-251, XP000182734.
Hyo-Kyung Han, "Targeted Prodrug Design to Optimize Drug Delivery", AAPS Pharmsci 2000, vol. 2, No. 1, Mar. 21, 2000, p. E6, XP-002289540.
European Search Report dated Jul. 23, 2004.
T. K. Burimova et al., "Preparation of Dipeptides of γ-Aminocarboxylic Acids," J. Org. Chem. USSR, vol. 8, 1972, pp. 541-543.
Lu et al., "Gabapentin Attenuates Nociceptive Behaviors in an Acute Arthritis Model in Rats", The Journal of Pharmacology and Experimental Therapeutics, vol. 290, No. 1, pp. 214-219, 1999.
Post, "Comparative Pharmacology of Bipolar Disorder and Schizophrenia", Schizophrenia Research, vol. 39, pp. 153-158, 1999.
Young et al., "Gabapentin as a Adjunctive Treatment in Bipolar Disorder", Journal of Affective Disorders, vol. 55, pp. 73-77, 1999.
Gareri et al., "Conventional and new Antidepressant Drugs in the Elderly", Progress in Neurobiology, vol. 61, pp. 353-396, 2000.
Altshuler et al., "Gabapentin in the Acute Treatment of Refractory Bipolar Disorder", Bipolar Disorders, vol. 1, pp. 61-65, 1999.
Bonnet et al., "Treatment of Alcohol Withdrawal Syndrome with Gabapentin", Pharmacopsychiatry, vol. 32, No. 3, pp. 107-109, May 1999.
Taylor, "Mechanisms of Action of Gabapentin", Rev. Neurol. (Paris), vol. 153, pp. 1S39-1S45, 1997.
Cory et al., "Potential Use of Gabapentin and Lamotrigine", The Annals of Pharmacotherapy, vol. 29, pp. 1160-1161, Nov. 1995.

* cited by examiner

AMINO ACID CONJUGATES PROVIDING FOR SUSTAINED SYSTEMIC CONCENTRATIONS OF GABA ANALOGUES

This application is a national stage entry under 35 U.S.C. § 371(c) of International Application No. PCT/US02/18493 filed Jun. 11, 2002, which claims priority under 35 U.S.C. § 119 to Provisional Application No. 60/297,732, filed in the United States on Jun. 11, 2001 and to Provisional Application No. 60/364,619, filed in the United States on Mar. 18, 2002, the entire contents of which are hereby incorporated by reference.

BACKGROUND OF THE INVENTION

1. Field of the Invention

This invention is directed to compounds that provide for sustained systemic concentrations of GABA analogs following administration to animals. This invention is also directed to pharmaceutical compositions including and methods using such compounds.

2. State of the Art

Rapid clearance of drugs from the systemic circulation represents a major impediment to effective clinical use of therapeutic and/or prophylactic compounds. Although multiple factors can influence the systemic concentrations of drugs achieved following administration (including drug solubility, dissolution rate, first-pass metabolism, p-glycoprotein and related efflux mechanisms, hepatic/renal elimination, etc), rapid systemic clearance is a particularly significant reason for suboptimal systemic exposure to many compounds. Rapid systemic clearance may require that large doses of drug be administered to achieve a therapeutic or prophylactic effect. Such larger doses of the drug, however, may result in greater variability in drug exposure, more frequent occurrence of side effects, or decrease in patient compliance. Frequent drug administration may also be required to maintain systemic drug levels above a minimum effective concentration. This problem is particularly significant for drugs that must be maintained in a well-defined concentration window to provide continuous therapeutic or prophylactic benefit while minimizing adverse effects (including for example, antibacterial agents, antiviral agents, anticancer agents, anticonvulsants, anticoagulants, etc.).

Conventional approaches to extend the systemic exposure of drugs with rapid clearance involve the use of formulation or device approaches that provide a slow or sustained release of drug within the intestinal lumen. These approaches are well known in the art and normally require that the drug be well absorbed from the large intestine, where such formulations are most likely to reside while releasing the drug. Drugs that are amenable to conventional sustained release approaches must be orally absorbed from the intestine and typically traverse this epithelial barrier by passive diffusion across the apical and basolateral membranes of the intestinal epithelial cells. The physicochemical features of a molecule that favor its passive uptake from the intestinal lumen into the systemic circulation include low molecular weight (e.g. <500 Da), adequate solubility, and a balance of hydrophobic and hydrophilic character (logP generally 1.5-4.0) (Navia and Chaturvedi, P. R. *Drug Discovery Today* 1996, 1, 179-189).

Polar or hydrophilic compounds are typically poorly absorbed through an animal's intestine as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluble vitamins, are polar compounds whose uptake is essential to the viability of the animal. For these substances there exist specific mechanisms for active transport of the solute molecules across the apical membrane of the intestinal epithelia. This transport is frequently energized by co-transport of ions down a concentration gradient. Solute transporter proteins are generally single sub-unit, multi-transmembrane spanning polypeptides, and upon binding of their substrates are believed to undergo conformational changes, which result in movement of the substrate(s) across the membrane.

Over the past 10-15 years, it has been found that a number of orally administered drugs are recognized as substrates by some of these transporter proteins, and that this active transport may largely account for the oral absorption of these molecules (Tsuji and Tamai, *Pharm. Res.* 1996, 13, 963-977). While in most instances the transporter substrate properties of these drugs were unanticipated discoveries made through retrospective analysis, it has been appreciated that, in principle, one might achieve good intestinal permeability for a drug by designing in recognition and uptake by a nutrient transport system. Drugs subject to active absorption in the small intestine are often unable to passively diffuse across epithelial cell membranes and are too large to pass through the tight junctions that exist between the intestinal cells. These drugs include many compounds structurally related to amino acids, dipeptides, sugars, nucleosides, etc. (for example, many cephalosporins, ACE inhibitors, AZT, etc).

Gamma ("γ")-aminobutyric acid ("GABA") is one of the major inhibitory transmitters in the central nervous system of mammals. GABA is not transported efficiently into the brain from the bloodstream (i.e., GABA does not effectively cross the blood-brain barrier). Consequently, brain cells provide virtually all of the GABA found in the brain (GABA is biosynthesized by decarboxylation of glutamic acid with pyridoxal phosphate).

GABA regulates neuronal excitability through binding to specific membrane proteins (i.e., GABAA receptors), which results in opening of an ion channel. The entry of chloride ion through the ion channel leads to hyperpolarization of the recipient cell, which consequently prevents transmission of nerve impulses to other cells. Low levels of GABA have been observed in individuals suffering from epileptic seizures, motion disorders (e.g., multiple sclerosis, action tremors, tardive dyskinesia), panic, anxiety, depression, alcoholism and manic behavior.

The implication of low GABA levels in a number of common disease states and/or common medical disorders has stimulated intensive interest in preparing GABA analogs, which have superior pharmaceutical properties in comparison to GABA (e.g. the ability to cross the blood brain barrier). Accordingly, a number of GABA analogs, with considerable pharmaceutical activity have been synthesized in the art (See, e.g., Satzinger et al, U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Application No. WO 92/09560; Silverman et al., International Application No. WO 93/23383; Horwell et al., International Application No. WO 97/29101, Horwell et al., International Application No. WO 97/33858; Horwell et al., International Application No. WO 97/33859; Bryans et al., International Application No. WO 98/17627; Guglietta et al., International Application No. WO 99/08671; Bryans et al., International Application No. WO 99/21824; Bryans et al., International Application No. WO 99/31057; Belliotti et al., International Application No. WO 99/31074; Bryans et al., International Application No. WO 99/31075; Bryans et al., International Application No. WO 99/61424; Bryans et al., International Application No. WO 00/15611; Bryans, International Application No. WO 00/31020; Bryans et al., International Application No. WO 00/50027; and Bryans et al, International Application No. WO 02/00209).

Pharmaceutically important GABA analogs include, for example, gabapentin, pregabalin, vigabatrin and baclofen. Gabapentin is a lipophilic GABA analog that can pass through the blood-brain barrier, which has been used to clinically treat epilepsy since 1994. Gabapentin also has potentially useful therapeutic effects in chronic pain states (e.g., neuropathic pain, muscular and skeletal pain), psychiatric disorders (e.g., panic, anxiety, depression, alcoholism and manic behavior), movement disorders (e.g., multiple sclerosis, action tremors, tardive dyskinesia), etc. (Magnus, *Epilepsia*, 1999, 40:S66-S72). Currently, gabapentin is also used in the clinical management of neuropathic pain. Pregabalin, which possesses greater potency in pre-clinical models of pain and epilepsy than gabapentin is presently in Phase III clinical trials.

Rapid systemic clearance is a significant problem with many GABA analogs including gabapentin, which consequently require frequent dosing to maintain a therapeutic or prophylactic concentration in the systemic circulation (Bryans et al., *Med. Res. Rev.*, 1999, 19, 149-177). For example, dosing regimens of 300-600 mg doses of gabapentin administered three times per day are typically used for anticonvulsive therapy. Higher doses (1800-3600 mg/day in divided doses) are typically used for the treatment of neuropathic pain states.

Sustained released formulations are a conventional solution to the problem of rapid systemic clearance, as is well known to those of skill in the art (See, e.g., "Remington's Pharmaceutical Sciences," Philadelphia College of Pharmacy and Science, 17th Edition, 1985). Osmotic delivery systems are also recognized methods for sustained drug delivery (See, e.g., Verma et al., *Drug Dev Ind. Pharm.*, 2000,26:695-708). Many GABA analogs, including gabapentin and pregabalin, are not absorbed via the large intestine. Rather, these compounds are typically absorbed in the small intestine by the large neutral amino acid transporter ("LNAA") (Jezyk et al., *Pharm. Res.*, 1999, 16, 519-526). The rapid passage of conventional dosage forms through the proximal absorptive region of the gastrointestinal tract has prevented the successful application of sustained release oral dosage technologies to GABA analogs. Thus, there is a significant need for effective sustained release versions of GABA analogs to minimize increased dosing frequency due to rapid systemic clearance of these compounds.

Another deficiency with some GABA analogs, including gabapentin, is their lack of dose-proportional oral bioavailability (see Radulovic et al, *Drug Metab. Dispos.* 1995, 23, 441-448; Gidal et al, *Epilepsy Res.* 2000, 40, 123-127; Gabapentin Supplementary Basis for Approval, Warner-Lambert, Inc.). Absorption of gabapentin in mammals is subject to saturation, since the large neutral amino acid transport system has limited substrate capacity and is localized to the upper part of the small intestine, creating an absorption window that restricts the ability of the drug to be taken up into the bloodstream. Thus in man, gabapentin oral bioavailability decreases from about 60% at a dose of 300 mg to about 35% at a dose of 1600 mg. This leads not only to inefficient use of the administered drug, but also to unpredictable and highly variable drug levels in patients, particularly at the higher doses associated with efficacy in the treatment of epilepsy and neuropathic pain (Gidal et al, *Epilepsy Res.* 1998, 31, 91-99). There is, therefore, a need for derivatives of gabapentin and other GABA analogs, which following oral administration to a patient in need of therapy provide therapeutically efficacious levels of the GABA analog in the plasma of a patient, where the concentration of the GABA analog in plasma of the patient over time provides a curve of concentration of the GABA analog in the plasma over time, the curve having an area under the curve (AUC) which is substantially more proportional to the dose of GABA analog administered, as compared to the proportionality achieved following oral administration of the GABA analog itself. There is similarly a need for derivatives of gabapentin and other GABA analogs, which following oral administration to a patient in need of therapy provide therapeutically efficacious levels of the GABA analog in the plasma of a patient, where the concentration of the GABA analog in plasma of the patient over time provides a curve of concentration of the GABA analog in the plasma over time, the curve having a maximum plasma concentration ($C_{max}$) which is substantially more proportional to the dose of GABA analog administered, as compared to the proportionality achieved following oral administration of the GABA analog itself.

One pathway that might provide for the sustained delivery of drugs with rapid systemic clearance is the proton-coupled peptide transport system (Leibach and Ganapathy, *Ann. Rev. Nutr.* 1996, 16, 99-119). These transporters mediate the cellular uptake of small intact peptides consisting of two or three amino acids and are found primarily in the intestine and kidney. In the intestine, where small peptides are not well-absorbed by passive diffusion, the transporters act as a vehicle for their effective absorption. Transporters in the kidney actively reabsorb di- and tri-peptides from the glomerular filtrate, thereby increasing their half-life in the circulation.

Two proton-coupled peptide transporters that have been cloned and characterized are PEPT1 and PEPT2. PEPT1 is a low-affinity, high-capacity transporter found primarily in the intestine. The human PEPT1 consists of 708 amino acids and possesses 12 putative transmembrane domains. PEPT2, in contrast, is a high-affinity, low-capacity transporter found mostly in the kidney. It consists of 729 amino acids and is 50% identical to human intestinal PEPT1.

Studies of PEPT1 and PEPT2 have shown that the transporters account for the absorption and reabsorption of certain therapeutically active compounds. The compounds include both biologically active peptides (e.g., renin inhibitors) and zwitterionic antibiotics. Based on these observations, researchers have suggested that peptide transporters, in conjunction with cytosolic peptidases, could be exploited for systemic delivery of certain drugs in the form of peptide prodrugs (see Tsuji and Tamai, *Pharm. Res.* 1996, 13, 963-977). Dipeptide analogues of α-methyldopa, L-α-methyldopa-Phe and L-α-methyldopa-Pro, for example, are absorbed more efficiently in the intestine than α-methyldopa alone. Once across the intestinal membrane, the dipeptides are hydrolyzed by cytosolic peptidases to release α-methyldopa.

Gallop et al have provided evidence from transporter mRNA expression profiling studies that PEPT expression in rat and human extends broadly over the length of the intestine, including the colon (U.S. Patent Application Ser. No. 60/351, 808 filed 24 Jan. 2002). They have suggested that sustained exposure to a substrate for a PEPT transporter could be achieved by formulating such a compound in an extended-release dosage form, which would gradually release the compound during transit of the formulation through the large intestine.

Peptide prodrug derivatives of gabapentin and other GABA analog drugs are contemplated by Bryans et al (see International Application No. WO 01/90052; U.K. Application GB 2,362,646; European Application EP 1,178,034). These workers have disclosed gabapentin derivatives wherein the amino group is blocked with particular α-aminoacyl or dipeptide moieties. More specifically, the α-amino acids comprising these peptide prodrug derivatives are the 20 naturally encoded α-amino acids, plus phenylglycine.

Prodrug derivatives of gabapentin and other GABA analog drugs are also disclosed by Gallop et al (see the co-pending International Applications WO 02/28881, WO 02/28883, WO 02/28411 and WO 02/32376). The compounds disclosed therein are bile acid conjugates of GABA analogs that are designed to be actively transported across the intestinal mucosa via interaction with the ileal bile acid transporter. These conjugates are further designed to undergo enterohepatic recirculation and to slowly release the parent GABA analog into the systemic circulation. Additional prodrug derivatives of gabapentin and other GABA analog drugs are disclosed by Gallop et al (see the co-pending International Application WO 02/42414). The compounds disclosed therein are α-aminoacyl and β-aminoacyl conjugates of GABA analogs that are designed to be actively absorbed across the intestinal mucosa via interaction with peptide transporters expressed in the intestine.

SUMMARY OF THE INVENTION

This invention is directed to the surprising discovery that PEPT1 and PEPT2 oligopeptide transporters can be utilized to provide sustained systemic concentrations of drugs administered to an animal. This invention, therefore, permits sustained therapeutic or prophylactic systemic blood concentrations of GABA analogues which heretofore could not be achieved. The present invention addresses the deficiencies of known GABA analogs by providing prodrugs of GABA analogs, and compositions of prodrugs of GABA analogs and methods for making prodrugs of GABA analogs. The present invention also provides methods for using prodrugs of GABA analogs and methods for using compositions of prodrugs of GABA analogs for treating or preventing common diseases and/or disorders. The prodrugs of the present invention are substrates for peptide transporters (PEPT1 and/or PEPT2) expressed in the mammalian gastrointestinal tract. This invention also provides sustained release dosage formulations containing prodrugs of GABA analogs that are substrates for peptide transporters, and the use of such formulations to minimize the frequency of dosing necessary to treat patients in need of GABA analog therapy.

Accordingly, in one of its aspects, this invention is directed to a compound of Formula (I):

wherein:
H is hydrogen;
I is —[NR$^{50}$—(CR$^{51}$R$^{52}$)$_a$—(CR$^{53}$R$^{54}$)$_b$—C(O)]—;
J is —[NR$^{55}$—(CR$^{56}$R$^{57}$)$_c$—(CR$^{58}$R$^{59}$)$_d$—C(O)]—;
K is —[NR$^{60}$—(CR$^{61}$R$^{62}$)$_e$—(CR$^{63}$R$^{64}$)$_f$—C(O)]—;
wherein a, b, c, d, e and f are independently 0 or 1, provided that at least one of a and b is 1, at least one of c and d is 1, and at least one of e and f is 1;
and wherein i, j and k are independently 0 or 1, provided that at least one of i, j and k is 1;
D is a moiety derived from a GABA analog having the following structure:

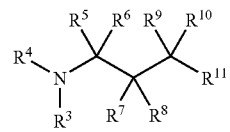

wherein:
R$^3$ is a covalent bond linking the GABA analog moiety to J$_j$;
R$^4$ is hydrogen, or R$^4$ and R$^9$ together with the atoms to which they are attached form an azetidine, substituted azetidine, pyrrolidine or substituted pyrrolidine ring;
R$^5$ and R$^6$ are independently selected from the group consisting of hydrogen, alkyl, substituted alkyl, alkenyl, substituted alkenyl, alkynyl, aryl, substituted aryl, heteroaryl and substituted heteroaryl;
R$^7$ and R$^8$ are independently selected from the group consisting of hydrogen, alkyl, substituted alkyl, alkenyl, alkynyl, aryl, substituted aryl, heteroaryl and substituted heteroaryl, or R$^7$ and R$^8$ together with the atoms to which they are attached form a cycloalkyl, substituted cycloalkyl, heterocyclic or substituted heterocyclic ring;
R$^9$ is selected from the group consisting of hydrogen, alkyl, substituted alkyl, alkenyl, alkynyl, aryl, substituted aryl, heteroaryl and substituted heteroaryl;
R$^{10}$ is selected from the group consisting of hydrogen, alkyl, substituted alkyl, alkenyl, alkynyl, aryl, substituted aryl, heteroaryl and substituted heteroaryl;
R$^{11}$ is C(O)R$^{12}$, wherein R$^{12}$ is a covalent bond linking the GABA analog moiety to K$_k$;
R$^{50}$ is hydrogen, alkyl, substituted alkyl, alkenyl, substituted alkenyl, alkynyl, aryl, substituted aryl, heteroaryl, substituted heteroaryl or R$^{50}$ and R$^{51}$ together with the atoms to which they are attached form a heterocyclyl ring;
R$^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{51}$ and R$^{52}$ together with the atoms to which they are attached form a cycloalkyl, substituted cycloalkyl, heterocyclyl or substituted heterocyclyl ring, or R$^{51}$ and R$^{53}$ together with the atoms to which they are attached form a cycloalkyl, substituted cycloalkyl, heterocyclyl or substituted heterocyclyl ring;
R$^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{53}$ and R$^{54}$ together with the atoms to which they are attached form a cycloalkyl, substituted cycloalkyl, heterocyclyl or substituted heterocyclyl ring;
R$^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^{55}$ is hydrogen, alkyl, substituted alkyl, alkenyl, substituted alkenyl, alkynyl, aryl, substituted aryl, heteroaryl, substituted heteroaryl or R$^{55}$ and R$^{56}$, together with the atoms to which they are attached form a heterocyclyl ring;

$R^{56}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{56}$ and $R^{57}$ together with the atoms to which they are attached form a cycloalkyl, substituted cycloalkyl, heterocyclyl or substituted heterocyclyl ring, or $R^{56}$ and $R^{58}$ together with the atoms to which they are attached form a cycloalkyl, substituted cycloalkyl, heterocyclyl or substituted heterocyclyl ring;

$R^{57}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{58}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{58}$ and $R^{59}$ together with the atoms to which they are attached form a cycloalkyl, substituted cycloalkyl, heterocyclyl or substituted heterocyclyl ring;

$R^{59}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{60}$ is hydrogen, alkyl, substituted alkyl, alkenyl, substituted alkenyl, alkynyl, aryl, substituted aryl, heteroaryl, substituted heteroaryl or $R^{60}$ and $R^{61}$, together with the atoms to which they are attached form a heterocyclyl ring;

$R^{61}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{61}$ and $R^{62}$ together with the atoms to which they are attached form a cycloalkyl, substituted cycloalkyl, heterocyclyl or substituted heterocyclyl ring, or $R^{61}$ and $R^{63}$ together with the atoms to which they are attached form a cycloalkyl, substituted cycloalkyl, heterocyclyl or substituted heterocyclyl ring;

$R^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{63}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{63}$ and $R^{64}$ together with the atoms to which they are attached form a cycloalkyl, substituted cycloalkyl, heterocyclyl or substituted heterocyclyl ring;

$R^{64}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

and pharmaceutically acceptable salts, hydrates and solvates thereof, provided that if k is 0 then neither I nor J is derived from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or phenylglycine;

and provided that when $R^5$, $R^6$, $R^9$ and $R^{10}$ are each hydrogen, then $R^7$ and $R^8$ are neither both hydrogen nor both methyl;

and yet further provided that when D is either of the following moieties

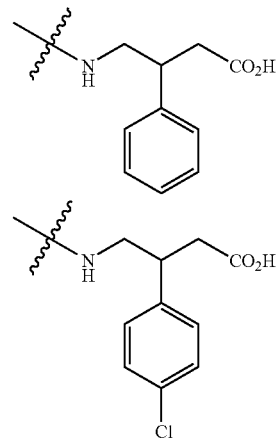

neither I nor J are selected from a group of moieties selected from the following moieties: $H_2NCH_2C(O)-$, $H_2NCH(CH_3)C(O)-$, $NH_2CH_2CH_2C(O)-$ and

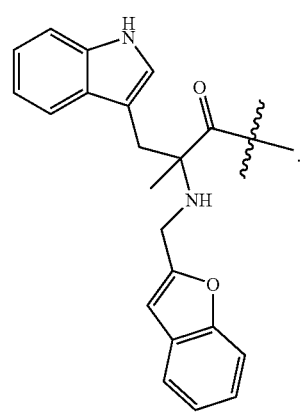

In a preferred embodiment, the compound of Formula (I) is sufficiently stable such that less than 50% of the compound is metabolized after incubation in vitro with Caco-2 homogenate for 1 hour, as described in more detail in Example 6.

In another aspect, this invention is directed to a pharmaceutical composition comprising a therapeutically effective amount of a compound of Formula (I) and a pharmaceutically acceptable carrier. The pharmaceutical composition may be used to treat or prevent epilepsy, depression, anxiety, psychosis, faintness attacks, hypokinesia, cranial disorders, neurodegenerative disorders, panic, pain (especially neuropathic pain, muscular pain or skeletal pain), inflammatory disease, insomnia, gastrointestinal disorders or ethanol withdrawal syndrome in a patient.

In another aspect, this invention is directed to sustained release oral dosage forms comprising a therapeutically effective amount of a compound of Formula (I) and, optionally, a pharmaceutically acceptable carrier.

In another aspect, this invention is directed to a method for treating or preventing epilepsy, depression, anxiety, psychosis, faintness attacks, hypokinesia, cranial disorders, neurodegenerative disorders, panic, pain (especially neuropathic pain, muscular pain or skeletal pain), inflammatory disease, insomnia, gastrointestinal disorders or ethanol withdrawal syndrome in a patient. The method comprises administering to a patient in need of such therapy a therapeutically effective amount of a compound of Formula (I), optionally with a pharmaceutically acceptable carrier.

In another aspect, this invention is directed to a method for achieving sustained release of a GABA analog in a patient in need of therapy. The method comprises orally administering to the patient a sustained release dosage form containing a therapeutically effective amount of a compound of Formula (I), and optionally, a pharmaceutically acceptable carrier.

In yet another aspect, this invention is directed to a method for achieving improved dose-proportional exposure of a GABA analog in a patient, said method comprising orally administering to the patient a therapeutically effective amount of a compound of Formula (I) and, optionally, a pharmaceutically acceptable carrier.

DETAILED DESCRIPTION OF THE INVENTION

Figure 1:
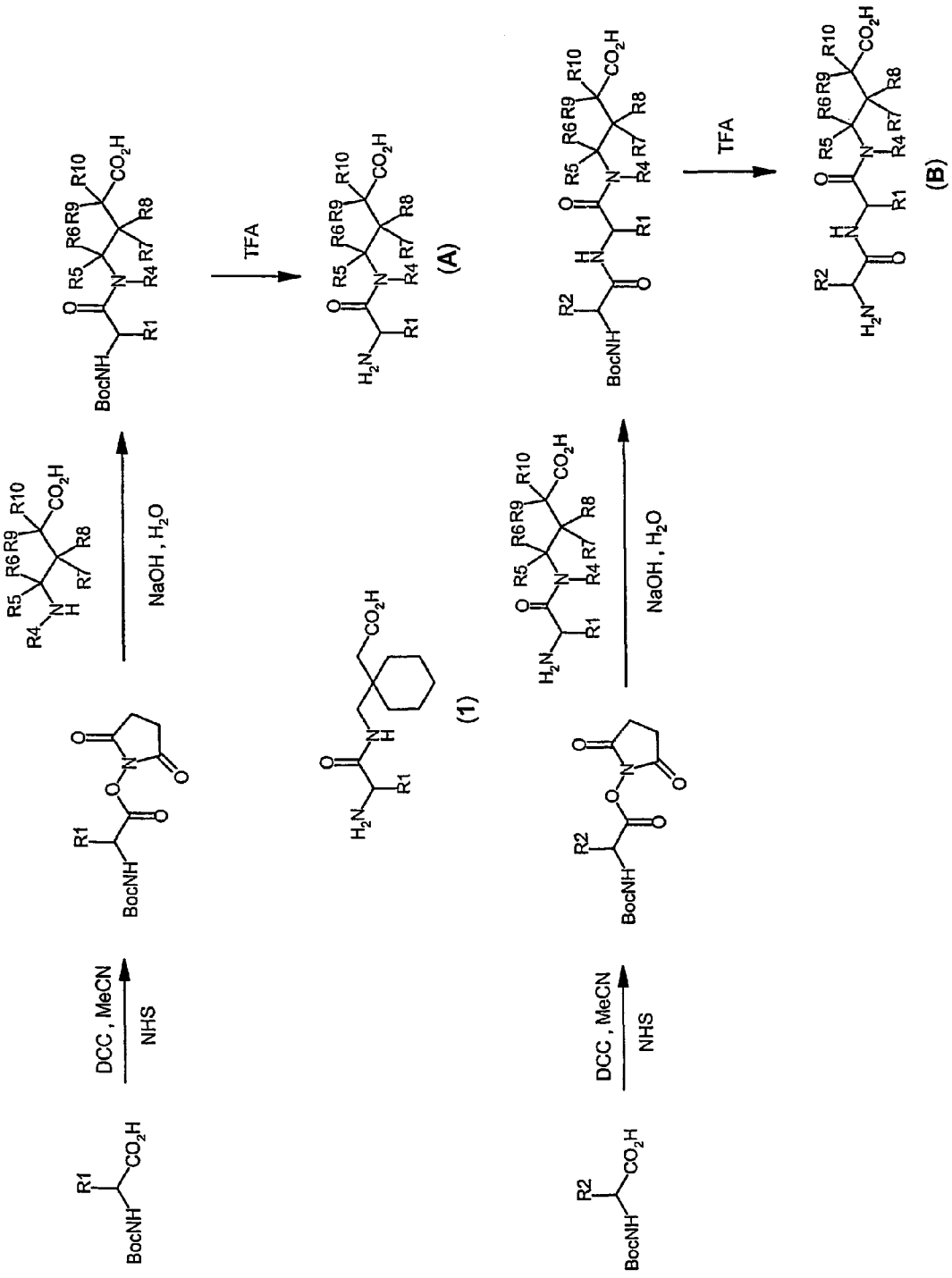
FIG. 1 illustrates the synthesis of aminoacyl and other peptide derivatives of GABA analogs.

This invention is directed to compounds that provide for sustained systemic concentrations of GABA analogues or active metabolites thereof following administration to animals. This invention is also directed to methods using the compounds and pharmaceutical compositions that are used in such methods. However, prior to describing this invention in further detail, the following terms will first be defined:

Definitions

As used herein, the term "animal" refers to various species such as mammalian and avian species including, by way of example, humans, cattle, sheep, horses, dogs, cats, turkeys, chicken, and the like. Preferably, the animal is a mammal and even more preferably is a human.

"Administering to the animal" refers to delivering a compound of Formula (I) to an animal through a suitable route. Such routes include, for example, oral, rectal, subcutaneous, intravenous, intramuscular and intranasal. Preferably, the compound is orally administered to the animal.

"Orally delivered" and "orally administered" refer to compounds, compositions and/or dosage forms which are administered to an animal in an oral form, preferably, in a pharmaceutically acceptable diluent. Oral delivery includes ingestion of the compounds, compositions and/or dosage forms, as well as oral gavage of the compounds and compositions.

"PEPT1 oligopeptide transporter" refers to a type of protein that absorbs peptides in certain tissues, such as the intestine. This transporter is described and characterized in the literature. See Adibi, S. A., *Gastroenterology* 1997, 113, 332-340 and Leibach et al., *Ann. Rev. Nutr.* 1996, 16, 99-119 for a discussion of the transporter.

"PEPT2 oligopeptide transporter" refers to a type of protein that absorbs peptides in certain tissues, such as the kidney. This transporter is described and characterized in the literature. See Dieck, S. T. et al., *GLIA* 1999, 25, 10-20, Leibach et al., *Ann. Rev. Nutr.* 1996, 16, 99-119; and Wong et al., *Am. J. Physiol.* 1998, 275, C967-C975 for a discussion of the transporter.

"Transported by either a PEPT1 or PEPT2 oligopeptide transporter" refers to the translocation of a molecule across a membrane of a cell expressing the transporter. The translocation occurs through interaction with the transporter and is energized by cotransport of $H^+$ ions across the membrane.

"Amino acid" is intended to denote α-amino acids and β-amino acids only.

α-Amino acids are molecules of the formula:

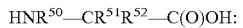

$HNR^{50}-CR^{51}R^{52}-C(O)OH$:

wherein:

$R^{50}$ is hydrogen, alkyl, substituted alkyl, alkenyl, substituted alkenyl, alkynyl, aryl, substituted aryl, heteroaryl, substituted heteroaryl or $R^{50}$ and $R^{51}$ together with the atoms to which they are attached form a heterocyclyl ring;

$R^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51}$ and $R^{52}$ together with the atoms to which they are attached form a cycloalkyl, substituted cycloalkyl, heterocyclyl or substituted heterocyclyl ring;

$R^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

β-Amino acids are molecules of formula:

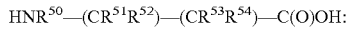

$HNR^{50}-(CR^{51}R^{52})-(CR^{53}R^{54})-C(O)OH$:

wherein:

$R^{50}$ is hydrogen, alkyl, substituted alkyl, alkenyl, substituted alkenyl, alkynyl, aryl, substituted aryl, heteroaryl, substituted heteroaryl or $R^{50}$ and $R^{51}$ together with the atoms to which they are attached form a heterocyclyl ring;

$R^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{51}$ and $R^{52}$ together with the atoms to which they are attached form a cycloalkyl, substituted cycloalkyl, heterocyclyl or substituted heterocyclyl ring, or $R^{51}$ and $R^{53}$ together with the atoms to which they are attached form a cycloalkyl, substituted cycloalkyl, heterocyclyl or substituted heterocyclyl ring;

$R^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{53}$ and $R^{54}$ together with the atoms to which they are attached form a cycloalkyl, substituted cycloalkyl, heterocyclyl or substituted heterocyclyl ring;

$R^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

"Naturally occurring amino acid" refers to any of the alpha-amino acids that are the chief components of proteins. The amino acids are either synthesized by living cells or are obtained as essential components of the diet. Such amino acids include, for example, the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"Derived from a compound" refers to a moiety that is structurally related to such a compound. The structure of the moiety is identical to the compound except at 1 or 2 positions. At these positions, either a hydrogen atom attached to a heteroatom or a hydroxyl moiety of a carboxylic acid group has been replaced with a covalent bond that serves as a point of attachment to another moiety. "Derived from an α-amino acid" is meant to specifically denote that the point of attachment is either the terminal α-amino group or the terminal α-acid group of the amino acid. For example, the moiety —NHCH$_2$C(O)— is derived from glycine. In the moiety, both a hydrogen atom on the amino group and a hydroxyl portion of the carboxyl group have been replaced with a covalent bond.

"GABA analog" refers to a compound of the following structure:

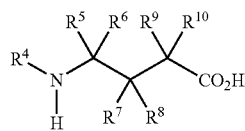

wherein $R^4$ is hydrogen, or $R^4$ and $R^9$ together with the atoms to which they are attached form an azetidine, substituted azetidine, pyrrolidine or substituted pyrrolidine ring;

$R^5$ and $R^6$ are independently selected from the group consisting of hydrogen, alkyl, substituted alkyl, alkenyl, substituted alkenyl, alkynyl, aryl, substituted aryl, heteroaryl and substituted heteroaryl;

$R^7$ and $R^8$ are independently selected from the group consisting of hydrogen, alkyl, substituted alkyl, alkenyl, alkynyl, aryl, substituted aryl, heteroaryl and substituted heteroaryl, or $R^7$ and $R^8$ together with the atoms to which they are attached form a cycloalkyl substituted cycloalkyl, heterocyclic or substituted heterocyclic ring;

$R^9$ is selected from the group consisting of hydrogen, alkyl, substituted alkyl, alkenyl, alkynyl, aryl, substituted aryl, heteroaryl and substituted heteroaryl; and, $R^{10}$ is selected from the group consisting of hydrogen, alkyl, substituted alkyl, alkenyl, alkynyl, aryl, substituted aryl, heteroaryl and substituted heteroaryl.

"Active metabolite of a drug" refers to products of in vivo modification of the drug which have therapeutic or prophylactic effect.

"Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

"Sustained release" refers to release of a drug or an active metabolite thereof into the systemic circulation over a prolonged period of time (typically periods of at least six hours) relative to that achieved by administration of a conventional immediate-release formulation of the drug.

"Conjugating" refers to the formation of a covalent bond.

"Active transport or active transport mechanism" refers to the movement of molecules across cellular membranes that: a) is directly or indirectly dependent on an energy mediated process (i.e. driven by ATP hydrolysis, ion gradient, etc); or b) occurs by facilitated diffusion mediated by interaction with specific transporter proteins; or c) occurs through a modulated solute channel.

"Amino-protecting group" or "amino-blocking group" refers to any group which when bound to one or more amino groups prevents reactions from occurring at these amino groups and which protecting groups can be removed by conventional chemical steps to reestablish the amino group. The particular removable blocking group is not critical and preferred amino blocking groups include, by way of example only, t-butyoxycarbonyl (t-BOC), benzyloxycarbonyl (CBZ), and the like.

"Carboxyl-protecting group" or "carboxyl-blocking group" refers to any group which when bound to one or more carboxyl groups prevents reactions from occurring at these groups and which protecting groups can be removed by conventional chemical steps to reestablish the carboxyl group. The particular removable blocking group is not critical and preferred carboxyl blocking groups include, by way of example only, esters of the formula —COOR″ where R″ is selected from the group consisting of alkyl, substituted alkyl, alkenyl, substituted alkenyl, aryl, substituted aryl, alkaryl, substituted alkaryl, cycloalkyl, substituted cycloalkyl, heteroaryl, substituted heteroaryl, heterocyclic, and substituted heterocyclic.

"AUC" is the area under the plasma drug concentration-versus-time curve extrapolated from zero time to infinity.

"$C_{max}$" is the highest drug concentration observed in plasma following an extravascular dose of drug.

"Prodrug" refers to a derivative of a drug molecule that requires a transformation within the body to release the active drug. Prodrugs are frequently (though not necessarily) pharmacologically inactive until converted to the parent drug. Typically, prodrugs are designed to overcome pharmaceutical and/or pharmacokinetically based problems associated with the parent drug molecule that would otherwise limit the clinical usefulness of the drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo. Ideally, the promoiety is rapidly cleared from the body upon cleavage from the prodrug.

"Dose-Proportional Drug Exposure" or "Dose-Proportionality" refers to the situation where either (i) the concentration of a drug in the plasma of an animal over time (at a therapeutically relevant level) provides a curve of concentration of the drug in the plasma over time, the curve having an area under the curve (AUC) which is substantially proportional to the dose of the drug administered; or (ii) the concentration of a drug in the plasma of an animal over time (at a therapeutically relevant level) provides a curve of concentration of the drug in the plasma over time, the curve having a maximum plasma concentration ($C_{max}$) which is substantially proportional to the dose of GABA analog administered.

"Alkyl" refers to alkyl groups preferably having from 1 to 20 carbon atoms and more preferably 1 to 6 carbon atoms. This term is exemplified by groups such as methyl, t-butyl, n-heptyl, octyl, dodecyl and the like.

"Substituted alkyl" refers to an alkyl group, preferably of from 1 to 20 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 20 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, -$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, -$SO_2$-heterocyclic, —$SO_2$-substituted heterocyclic and —$SO_2$NRR where R is hydrogen or alkyl.

"Alkenyloxy" refers to the group —O-alkenyl.

"Substituted alkenyloxy" refers to the group —O-substituted alkenyloxy.

"Alkynyl" refers to alkynyl group preferably having from 2 to 20 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Alkylene" refers to a divalent alkylene group preferably having from 1 to 20 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkenylene" refers to a divalent alkenylene group preferably having from 2 to 20 carbon atoms and more preferably 1 to 6 carbon atoms and having from 1 to 2 sites of alkenyl unsaturation. This term is exemplified by groups such as ethenylene (—CH═CH—), propenylene (—CH$_2$CH═CH—), and the like.

"Substituted alkenylene" refers to alkenylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynylene" refers to a divalent alkynylene group preferably having from 2 to 20 carbon atoms and more preferably 1 to 6 carbon atoms and having from 1 to 2 sites of alkynyl unsaturation. This term is exemplified by groups such as ethynylene, propynylene and the like.

"Substituted alkynylene" refers to alkynylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(═NH)— and the term "alkylamidino" refers to compounds having 1 to 3 alkyl groups (e.g., alkylHNC(═NH)—).

"Thioamidino" refers to the group RSC(═NH)— where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7 yl, and the like). Preferred aryls include phenyl and naphthyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Arylene" refers to a divalent unsaturated aromatic carbocyclic group of from 6 to 14 carbon atoms having a single ring (e.g., phenylene) or multiple condensed rings (e.g., naphthylene or anthrylene) which condensed rings may or may not be aromatic. Preferred arylenes include phenylene and naphthylene. Substituted arylene refers to arylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 10 carbon atoms having a single cyclic ring including, by way of example, cyclopropyl, cyclobutyl, cyclopentyl, cyclohexyl, cyclooctyl and the like. This definition also includes bridged groups such as bicyclo[2.2.1]heptane and bicyclo[3.3.1]nonane.

"Cycloalkyloxy" refers to —O-cycloalkyl.

"Cycloalkenyl" refers to cyclic alkenyl groups of frm 3 to 10 carbon atoms having a single cyclic ring.

"Cycloalkenyloxy" refers to —O-cycloalkenyl.

"Substituted cycloalkyl" and "substituted cycloalkenyl" refers to an cycloalkyl or cycloalkenyl group, preferably, of from 3 to 10 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted cycloalkyloxy" and "substituted cycloalkenyloxy" refers to —O-substituted cycloalkyl and —O-substituted cycloalkenyloxy respectively.

"Cycloalkylene" refers to divalent cyclic alkylene groups of from 3 to 10 carbon atoms having a single cyclic ring including, by way of example, cyclopropylene, cyclobutylene, cyclopentylene, cyclooctylene and the like.

"Cycloalkenylene" refers to a divalent cyclic alkenylene groups of from 3 to 10 carbon atoms having a single cyclic ring.

"Substituted cycloalkylene" and "substituted cycloalkenylene" refers to a cycloalkylene or cycloalkenylene group, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC (=NR)NR-substituted aryl, —NRC(=NR)NR-cycloalkyl, —NRC(=NR)NR-heteroaryl, —NRC (=NR)NR-substituted heteroaryl, —NRC (=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"N,N-Dimethylcarbamyloxy" refers to the group —OC(O)N(CH$_3$)$_2$.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroarylene" refers to a divalent aromatic carbocyclic group of from 2 to 10 carbon atoms and 1 to 4 heteroatoms selected from the group consisting of oxygen, nitrogen and sulfur within the ring. Such heteroarylene groups can have a single ring (e.g., pyridylene or furylene) or multiple condensed rings (e.g., indolizinylene or benzothienylene). Preferred heteroarylenes include pyridylene, pyrrolylene, indolylene and furylene.

"Substituted heteroarylene" refers to heteroarylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, amninoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS (O)$_2$-substituted heterocyclic, —OSO$_2$—

NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted heteroarylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclene" refers to heterocyclene groups which are substituted with from 1 to 3 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted hetero cyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Amino" refers to the —NH$_2$ group. "Substituted amino" refers to the —NR'R" group wherein R' and R" are independently hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic, substituted heterocyclic or where R' and R", together with the nitrogen atom pendent thereto, form a heterocyclic ring.

"Pharmaceutically acceptable salt" refers to pharmaceutically acceptable salts of a compound of Formula (I), which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Pharmaceutically acceptable carrier" refers to a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Utility

The compounds and methods described herein provide for the sustained release of the GABA analog or active metabolite thereof relative to dosing with the parent drug itself. For example, a compound and/or composition of the invention is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome. Further, in certain embodiments, the compounds and/or compositions of the invention are administered to a patient, preferably a human, as a preventative measure against various diseases or disorders. Thus, the compounds and/or compositions of the invention may be administered as a preventative measure to a patient having a predisposition for epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome. Accordingly, the compounds and/or compositions of the invention may be used for the prevention of one disease or disorder and concurrently treating another (e.g., prevention of psychosis while treating gastrointestinal disorders; prevention of neuropathic pain while treating ethanol withdrawal syndrome).

The suitability of the compounds and/or compositions of the invention in treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be determined by methods described in the art (See, e.g., Satzinger et al., U.S. Pat. No. 4,024,175; Satzinger et al., U.S. Pat. No. 4,087,544; Woodruff, U.S. Pat. No. 5,084,479; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Application No. WO 92/09560; Silverman et al., International Application No. WO 93/23383; Horwell et al., International Application No. WO 97/29101, Horwell et al., International Application No. WO 97/33858; Horwell et al., International Application No. WO 97/33859; Bryans et al., International Application No. WO 98/17627; Guglietta et al., International Application No. WO 99/08671; Bryans et al., International Application No. WO 99/21824; Bryans et al, International Application No. WO 99/31057; Magnus-Miller et al., International Application No. WO 99/37296; Bryans et al., International Application No. WO 99/31075; Bryans et al., International Application No. WO 99/61424; Pande, International Application No. WO 00/23067; Bryans, International Application No. WO 00/31020; Bryans et al., International Application No. WO 00/50027; and Bryans et al, International Application No. WO 02/00209). Procedures for using the compounds and/or compositions of the invention for treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome have also been described in the art (see references above). Thus, it is well with the capability of those of skill in the art to assay and use the compounds and/or of the invention to treat epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome.

All of the amino acid linked drugs described herein can also be used as intermediates in order to couple them to bile acids as disclosed previously, as in U.S. Provisional Application No. 60/297,472; U.S. Provisional Application No. 60/249,804; and U.S. Provisional Application No. 60/297,594 (along with the counterpart PCT Applications WO02/28881; WO02/2883; and WO02/32376) show GABA analogs coupled to bile acids through amino acid linkages. U.S. Provisional Application No. 60/297,654 (with counterpart PCT Application WO02/28882) shows L-Dopa analogs coupled to bile acids through amino acid linkages. All of these applications are incorporated herein by reference in their entirety.

PREFERRED EMBODIMENTS

This invention facilitates sustained therapeutic or prophylactic systemic blood concentrations of GABA analogues which heretofore could not be achieved.

Accordingly, in one of its compound aspects, this invention is directed to a compound of Formula (I):

H—I$_i$—J$_j$—D—K$_k$—OH      (I)

wherein:

H is hydrogen;

I is —[NR$^{50}$—(CR$^{51}$R$^{52}$)$_a$—(CR$^{53}$R$^{54}$)$_b$—C(O)]—;

J is —[NR$^{55}$—(CR$^{56}$R$^{57}$)$_c$—(CR$^{58}$R$^{59}$)$_d$—C(O)]—;

K is —[NR$^{60}$—(CR$^{61}$R$^{62}$)$_e$—(CR$^{63}$R$^{64}$)$_f$—C(O)]—;

wherein a, b, c, d, e and f are independently 0 or 1, provided that at least one of a and b is 1, at least one of c and d is 1, and at least one of e and f is 1;

and wherein i, j and k are independently 0 or 1, provided that at least one of i, j and k is 1;

D is a moiety derived from a GABA analog having the following structure:

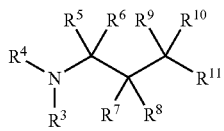

wherein

R$^3$ is a covalent bond linking the GABA analog moiety to J$_j$;

R$^4$ is hydrogen, or R$^4$ and R$^9$ together with the atoms to which they are attached form an azetidine, substituted azetidine, pyrrolidine or substituted pyrrolidine ring;

R$^5$ and R$^6$ are independently selected from the group consisting of hydrogen, alkyl, substituted alkyl, alkenyl, substituted alkenyl, alkynyl, aryl, substituted aryl, heteroaryl and substituted heteroaryl;

R$^7$ and R$^8$ are independently selected from the group consisting of hydrogen, alkyl, substituted alkyl, alkenyl, alkynyl, aryl, substituted aryl, heteroaryl and substituted heteroaryl, or R$^7$ and R$^8$ together with the atoms to which they are attached form a cycloalkyl, substituted cycloalkyl, heterocyclic or substituted heterocyclic ring;

R$^9$ is selected from the group consisting of hydrogen, alkyl, substituted alkyl, alkenyl, alkynyl, aryl, substituted aryl, heteroaryl and substituted heteroaryl;

R$^{10}$ is selected from the group consisting of hydrogen, alkyl, substituted alkyl, alkenyl, alkynyl, aryl, substituted aryl, heteroaryl and substituted heteroaryl;

R$^{11}$ is C(O)R$^{12}$, wherein R$^{12}$ is a covalent bond linking the GABA analog moiety to K$_k$;

R$^{50}$ is hydrogen, alkyl, substituted alkyl, alkenyl, substituted alkenyl, alkynyl, aryl, substituted aryl, heteroaryl, substituted heteroaryl or R$^{50}$ and R$^{51}$ together with the atoms to which they are attached form a heterocyclyl ring;

R$^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{51}$ and R$^{52}$ together with the atoms to which they are attached form a cycloalkyl, substituted cycloalkyl, heterocyclyl or substituted heterocyclyl ring, or R$^{51}$ and R$^{53}$ together with the atoms to which they are attached form a cycloalkyl, substituted cycloalkyl, heterocyclyl or substituted heterocyclyl ring;

R$^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{53}$ and R$^{54}$ together with the atoms to which they are attached form a cycloalkyl, substituted cycloalkyl, heterocyclyl or substituted heterocyclyl ring;

R$^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{55}$ is hydrogen, alkyl, substituted alkyl, alkenyl, substituted alkenyl, alkynyl, aryl, substituted aryl, heteroaryl, substituted heteroaryl or R$^{55}$ and R$^{56}$, together with the atoms to which they are attached form a heterocyclyl ring;

R$^{56}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{56}$ and R$^{57}$ together with the atoms to which they are attached form a cycloalkyl, substituted cycloalkyl, heterocyclyl or substituted heterocyclyl ring, or R$^{56}$ and R$^{58}$ together with the atoms to which they are attached form a cycloalkyl, substituted cycloalkyl, heterocyclyl or substituted heterocyclyl ring;

R$^{57}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{58}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{58}$ and $R^{59}$ together with the atoms to which they are attached form a cycloalkyl, substituted cycloalkyl, heterocyclyl or substituted heterocyclyl ring;

$R^{59}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{60}$ is hydrogen, alkyl, substituted alkyl, alkenyl, substituted alkenyl, alkynyl, aryl, substituted aryl, heteroaryl, substituted heteroaryl or $R^{60}$ and $R^{61}$, together with the atoms to which they are attached form a heterocyclyl ring;

$R^{61}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{61}$ and $R^{62}$ together with the atoms to which they are attached form a cycloalkyl, substituted cycloalkyl, heterocyclyl or substituted heterocyclyl ring, or $R^{61}$ and $R^{63}$ together with the atoms to which they are attached form a cycloalkyl, substituted cycloalkyl, heterocyclyl or substituted heterocyclyl ring;

$R^{62}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

$R^{63}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or $R^{63}$ and $R^{64}$ together with the atoms to which they are attached form a cycloalkyl, substituted cycloalkyl, heterocyclyl or substituted heterocyclyl ring;

$R^{64}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

and pharmaceutically acceptable salts, hydrates, and solvates thereof, provided that if k is 0 then neither I nor J is derived from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or phenylglycine;

and provided that when $R^5$, $R^6$, $R^9$ and $R^{10}$ are each hydrogen, then $R^7$ and $R^8$ are neither both hydrogen nor both methyl;

and yet further provided that when D is either of the following moieties

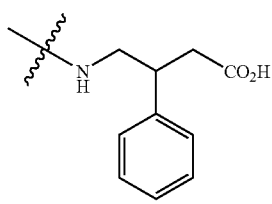

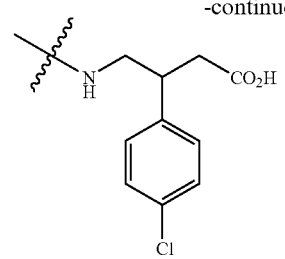

neither I nor J are selected from the group of moieties consisting of $H_2NCH_2C(O)$—, $H_2NCH(CH_3)C(O)$—, $NH_2CH_2CH_2C(O)$— and

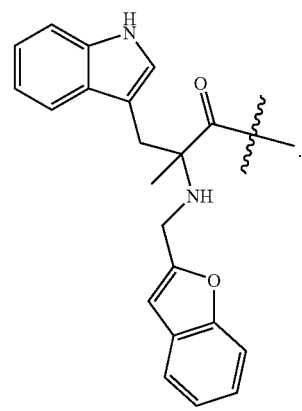

Preferably, in a compound of Formula (I), k is 0 and j is 1.

Preferably, D in a compound of Formula (I) is a moiety selected from a group consisting of the following GABA analog moieties:

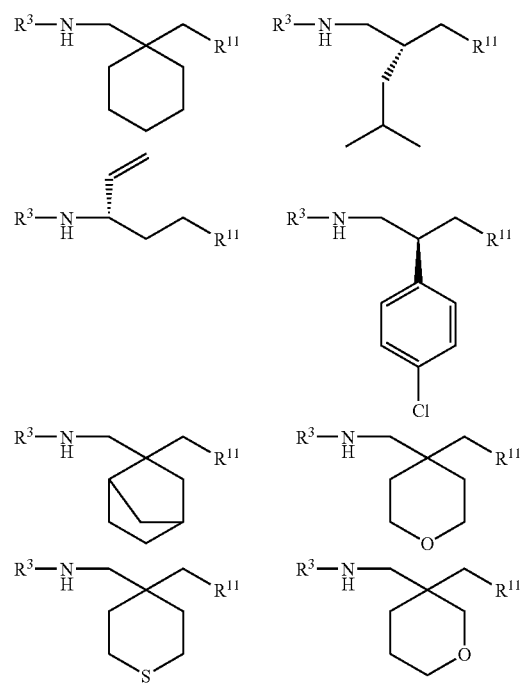

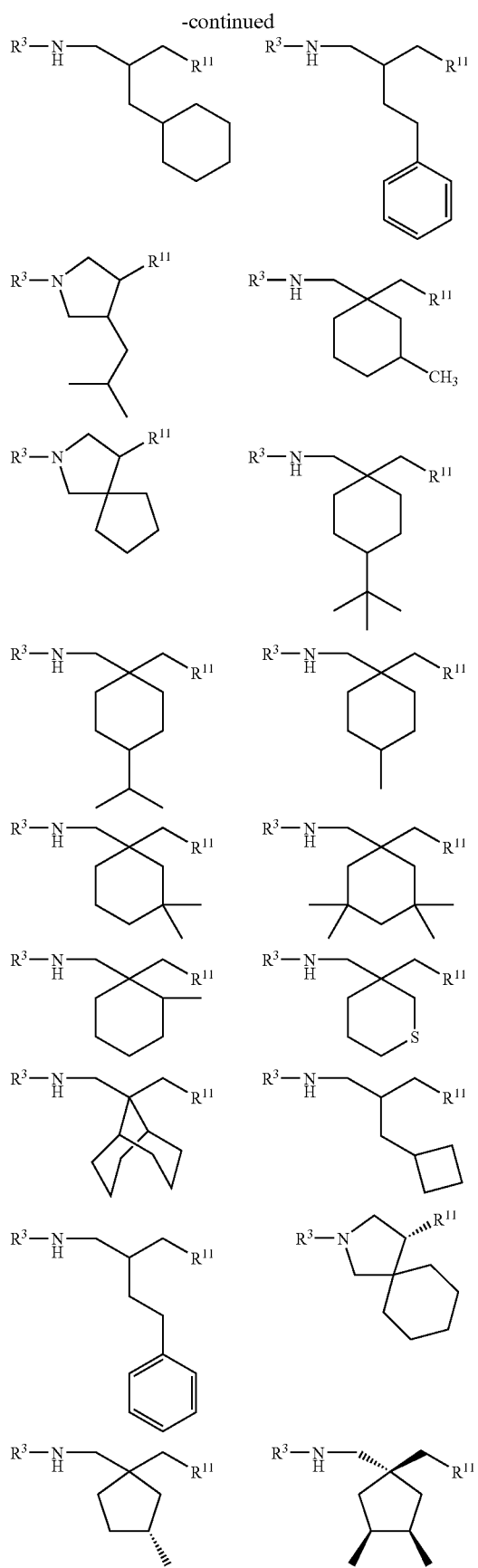

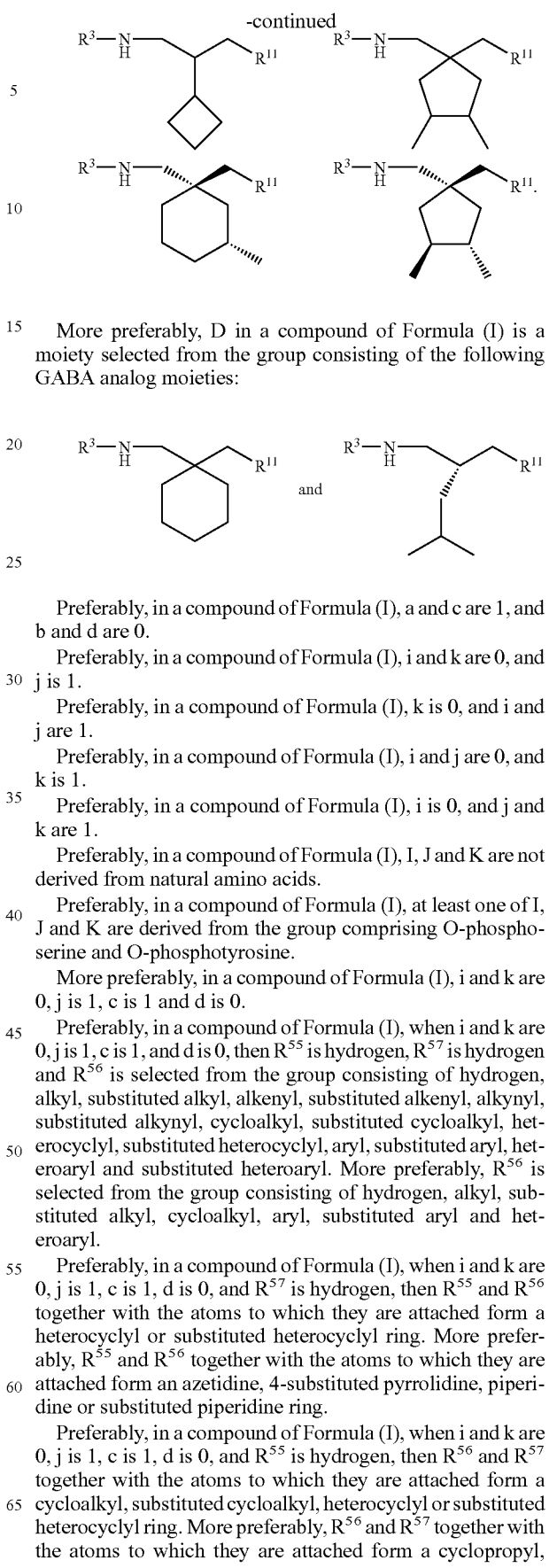

More preferably, D in a compound of Formula (I) is a moiety selected from the group consisting of the following GABA analog moieties:

Preferably, in a compound of Formula (I), a and c are 1, and b and d are 0.

Preferably, in a compound of Formula (I), i and k are 0, and j is 1.

Preferably, in a compound of Formula (I), k is 0, and i and j are 1.

Preferably, in a compound of Formula (I), i and j are 0, and k is 1.

Preferably, in a compound of Formula (I), i is 0, and j and k are 1.

Preferably, in a compound of Formula (I), I, J and K are not derived from natural amino acids.

Preferably, in a compound of Formula (I), at least one of I, J and K are derived from the group comprising O-phosphoserine and O-phosphotyrosine.

More preferably, in a compound of Formula (I), i and k are 0, j is 1, c is 1 and d is 0.

Preferably, in a compound of Formula (I), when i and k are 0, j is 1, c is 1, and d is 0, then $R^{55}$ is hydrogen, $R^{57}$ is hydrogen and $R^{56}$ is selected from the group consisting of hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl. More preferably, $R^{56}$ is selected from the group consisting of hydrogen, alkyl, substituted alkyl, cycloalkyl, aryl, substituted aryl and heteroaryl.

Preferably, in a compound of Formula (I), when i and k are 0, j is 1, c is 1, d is 0, and $R^{57}$ is hydrogen, then $R^{55}$ and $R^{56}$ together with the atoms to which they are attached form a heterocyclyl or substituted heterocyclyl ring. More preferably, $R^{55}$ and $R^{56}$ together with the atoms to which they are attached form an azetidine, 4-substituted pyrrolidine, piperidine or substituted piperidine ring.

Preferably, in a compound of Formula (I), when i and k are 0, j is 1, c is 1, d is 0, and $R^{55}$ is hydrogen, then $R^{56}$ and $R^{57}$ together with the atoms to which they are attached form a cycloalkyl, substituted cycloalkyl, heterocyclyl or substituted heterocyclyl ring. More preferably, $R^{56}$ and $R^{57}$ together with the atoms to which they are attached form a cyclopropyl, cyclobutyl, cyclopentyl, substituted cyclopentyl, cyclohexyl, substituted cyclohexyl, piperidinyl or substituted piperidinyl ring.

In one embodiment of a compound of Formula (I), when i and k are 0, j is 1, c is 1, d is 0, $R^{55}$ is hydrogen, $R^{57}$ is hydrogen and $R^{56}$ is substituted alkyl, then preferably $R^{56}$ is selected from the group consisting of arylalkyl, substituted arylalkyl, heteroarylalkyl and substituted heteroarylalkyl. More preferably, $R^{56}$ is selected from the group consisting of substituted benzyl, s-naphthylmethyl, substituted s-naphthylmethyl, t-pyridylmethyl, substituted t-pyridylmethyl, t-quinolylmethyl, substituted t-quinolylmethyl, u-furanylmethyl, substituted u-furanylmethyl, u-benzofuranylmethyl, substituted u-benzofuranylmethyl, u-thienylmethyl, substituted u-thienylmethyl, u-benzothienylmethyl, substituted u-benzothienylmethyl, u-pyrrolylmethyl, substituted u-pyrrolylmethyl, substituted u-indolylmethyl, u-pyrazinylmethyl, substituted u-pyrazinylmethyl, substituted v-imidazolylmethyl, v-oxazolylmethyl, substituted v-oxazolylmethyl, v-thiazolylmethyl and substituted v-thiazolylmethyl, wherein s is 1 or 2; t is 2, 3 or 4; u is 2 or 3; and v is 2, 4 or 5. Even more preferably $R^{56}$ is selected from the group consisting of 2-methylphenylmethyl, 3-methylphenylmethyl, 4-methylphenylmethyl, 2-methoxyphenylmethyl, 3-methoxyphenylmethyl, 4-methoxyphenylmethyl, 2-trifluoromethylphenylmethyl, 3-trifluoromethylphenylmethyl, 4-trifluoromethylphenylmethyl, 2-cyanophenylmethyl, 3-cyanophenylmethyl, 4-cyanophenylmethyl, 2-fluorophenylmethyl, 3-fluorophenylmethyl, 4-fluorophenylmethyl, 2-chlorophenylmethyl, 3-chlorophenylmethyl, 4-chlorophenylmethyl, 2-bromophenylmethyl, 3-bromophenylmethyl, 4-bromophenylmethyl, 2-iodophenylmethyl, 3-iodophenylmethyl, 4-iodophenylmethyl, 2,3-difluorophenylmethyl, 2,4-difluorophenylmethyl, 2,5-difluorophenylmethyl, 2,6-difluorophenylmethyl, 3,4-difluorophenylmethyl, 3,5-difluorophenylmethyl, 2,3-dichlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 1-naphthylmethyl, 2-naphthylmethyl, 2-pyridylmethyl, 3-pyridylmethyl, 4-pyridylmethyl, 2-quinolylmethyl, 3-quinolylmethyl, 4-quinolylmethyl, 2-furanylmethyl, 3-furanylmethyl, 3-benzofuranylmethyl, 2-thienylmethyl, 3-thienylmethyl, 3-benzothienylmethyl, 5-hydroxyindol-3-ylmethyl, 5-alkoxyindol-3-ylmethyl, 5-acyloxyindol-3-ylmethyl, 2-oxazolylmethyl, 4-oxazolylmethyl 2-thiazolylmethyl and 4-thiazolylmethyl.

In another embodiment of a compound of Formula (I), when i and k are 0, j is 1, c is 1, d is 0, $R^{55}$ is hydrogen, $R^{57}$ is hydrogen and $R^{56}$ is substituted alkyl, then preferably $R^{56}$ is selected from the group consisting of —$(CH_2)_nC(O)XR^{13}$ and —$CH_2[4—C_6H_4—OC(O)R^{15}]$, wherein:

n is 1 or 2;

X is O or $NR^{14}$;

$R^{13}$ and $R^{14}$ are independently selected from the group consisting of hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl, or $R^{13}$ and $R^{14}$ together with the atoms to which they are attached form a heterocyclyl or substituted heterocyclyl ring; and $R^{15}$ is selected from the group consisting of hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, alkoxy, substituted alkoxy, alkenyloxy, substituted alkenyloxy, alkynyloxy, substituted alkynyloxy, cycloalkoxy, substituted cycloalkoxy, heterocyclyloxy, substituted heterocyclyloxy, aryloxy, substituted aryloxy, heteroaryloxy and substituted heteroaryloxy;

with the provisos that when X is O, then $R^{13}$ is not hydrogen; and when X is $NR^{14}$, then $R^{13}$ and $R^{14}$ are not both hydrogen.

Preferred compounds of Formula (I) are compounds selected from the group consisting of L-1-Naphthylalanine-Gabapentin, L-2-Naphthylalanine-Gabapentin, L-2-Quinoylalanine-Gabapentin, L-(2-Quinoylalanine N-Oxide)-Gabapentin, L-2-Pyridylalanine-Gabapentin, L-3-Pyridylalanine-Gabapentin, L-(4-Pyridylalanine N-Oxide)-Gabapentin, L-2-Thienylalanine-Gabapentin, L-3-Thienylalanine-Gabapentin, L-3-Benzothienylalanine-Gabapentin, L-4-Thiazolylalanine-Gabapentin, L-2-Methylphenylalanine-Gabapentin, L-4-Methylphenylalanine-Gabapentin, L-2-Trifluoromethylphenylalanine-Gabapentin, L-3-Trifluoromethylphenylalanine-Gabapentin, L-4-Trifluoromethylphenylalanine-Gabapentin, L-2-Fluorophenylalanine-Gabapentin, L-3-Fluorophenylalanine-Gabapentin, L-4-Fluorophenylalanine-Gabapentin, L-2-Chlorophenylalanine-Gabapentin, L-3-Chlorophenylalanine-Gabapentin, L-4-Chlorophenylalanine-Gabapentin, L-4-Bromophenylalanine-Gabapentin, L-4-Iodophenylalanine-Gabapentin, L-2-Methoxyphenylalanine-Gabapentin, L-4-Methoxyphenylalanine-Gabapentin, L-4-Ethoxyphenylalanine-Gabapentin, L-3-Cyanophenylalanine-Gabapentin, L-4-Cyanophenylalanine-Gabapentin, L-3,4-Difluorophenylalanine-Gabapentin, L-3,5-Difluorophenylalanine-Gabapentin, D, L-2,4-Difluorophenylalanine-Gabapentin, D, L-2,6-Difluorophenylalanine-Gabapentin, L-2,4-Dichlorophenylalanine-Gabapentin, L-3,4-Dichlorophenylalanine-Gabapentin, L-Pipecolyl-Gabapentin, L-tert-Butylglycine-Gabapentin, L-2,3-Diaminopropionyl-Gabapentin, L-Norvaline-Gabapentin, L-Penicillamine-Gabapentin, 1-Aminocyclopropane-1-Carbonyl-Gabapentin, 1-Aminocyclohexane-1-Carbonyl-Gabapentin, L-Homophenylalanine-Gabapentin, L-Aspartyl-β-(Pyrrolidinyl)-Gabapentin, L-Aspartyl-β-(Butylamido)-Gabapentin, L-Aspartyl-β-(2-Methoxyethylamido)-Gabapentin, L-Aspartyl-β-(Piperidinyl)-Gabapentin, L-Aspartyl-β-(3-Methylbutylamido)-Gabapentin, L-Aspartyl-β-(Cyclohexylamido)-Gabapentin, L-Aspartyl-β-(4-Amidomethylpyridine)-Gabapentin, L-Aspartyl-β-(3-Amidomethylpyridine)-Gabapentin, L-Aspartyl-β-(Heptylamido)-Gabapentin, L-Aspartyl-β-(3,4-Dimethoxyphenethylamido)-Gabapentin, L-Aspartyl-β-(O-Cyclohexyl ester)-Gabapentin, L-Aspartyl-β-(O-Benzyl ester)-Gabapentin, L-Tyrosine-(O-2,6-Dimethylbenzoyl)-Gabapentin, L-Tyrosine-(O-2,6-Dimethoxybenzoyl)-Gabapentin, L-Tyrosine-(O-2-Methylbenzoyl)-Gabapentin, L-Tyrosine-(O-2-Bromobenzyloxycarbonyl)-Gabapentin, L-1-Naphthylalanine-Pregabalin, L-2-Naphthylalanine-Pregabalin, L-2-Quinoylalanine-Pregabalin, L-(2-Quinoylalanine N-Oxide)-Pregabalin, L-2-Pyridylalanine-Pregabalin, L-3-Pyridylalanine-Pregabalin, L-(4-Pyridylalanine N-Oxide)-Pregabalin, L-2-Thienylalanine-Pregabalin, L-3-Thienylalanine-Pregabalin, L-3-Benzothienylalanine-Pregabalin, L-4-Thiazolylalanine-Pregabalin, L-2-Methylphenylalanine-Pregabalin, L-4-Methylphenylalanine-Pregabalin, L-2-Trifluoromethylphenylalanine-Pregabalin, L-3-Trifluoromethylphenylalanine-Pregabalin, L-4-

Trifluoromethylphenylalanine-Pregabalin, L-2-Fluorophenylalanine-Pregabalin, L-3-Fluorophenylalanine-Pregabalin, L-4-Fluorophenylalanine-Pregabalin, L-2-Chlorophenylalanine-Pregabalin, L-3-Chlorophenylalanine-Pregabalin, L-4-Chlorophenylalanine-Pregabalin, L-4-Bromophenylalanine-Pregabalin, L-4-Iodophenylalanine-Pregabalin, L-2-Methoxyphenylalanine-Pregabalin, L-4-Methoxyphenylalanine-Pregabalin, L-4-Ethoxyphenylalanine-Pregabalin, L-3-Cyanophenylalanine-Pregabalin, L-4-Cyanophenylalanine-Pregabalin, L-3,4-Difluorophenylalanine-Pregabalin, L-3,5-Difluorophenylalanine-Pregabalin, D, L-2,4-Difluorophenylalanine-Pregabalin, D, L-2,6-Difluorophenylalanine-Pregabalin, L-2,4-Dichlorophenylalanine-Pregabalin, L-3,4-Dichlorophenylalanine-Pregabalin, L-Pipecolyl-Pregabalin, L-tert-Butylglycine-Pregabalin, L-2,3-Diaminopropionyl-Pregabalin, L-Norvaline-Pregabalin, L-Penicillamine-Pregabalin, 1-Aminocyclopropane-1-Carbonyl-Pregabalin, 1-Aminocyclohexane-1-Carbonyl-Pregabalin, L-Homophenylalanine-Pregabalin, L-Aspartyl-β-(Pyrrolidinyl)-Pregabalin, L-Aspartyl-β-(Butylamido)-Pregabalin, L-Aspartyl-β-(2-Methoxyethylamido)-Pregabalin, L-Aspartyl-β-(Piperidinyl)-Pregabalin, L-Aspartyl-β-(3-Methylbutylamido)-Pregabalin, L-Aspartyl-β-(Cyclohexylamido)-Pregabalin, L-Aspartyl-β-(4-Amidomethylpyridine)-Pregabalin, L-Aspartyl-β-(3-Amidomethylpyridine)-Pregabalin, L-Aspartyl-β-(Heptylamido)-Pregabalin, L-Aspartyl-β-(3,4-Dimethoxyphenethylamido)-Pregabalin, L-Aspartyl-β-(O-Cyclohexyl ester)-Pregabalin, L-Aspartyl-β-(O-Benzyl ester)-Pregabalin, L-Tyrosine-(O-2,6-Dimethylbenzoyl)-Pregabalin, L-Tyrosine-(O-2,6-Dimethoxybenzoyl)-Pregabalin, L-Tyrosine-(O-2-Methylbenzoyl)-Pregabalin and L-Tyrosine-(O-2-Bromobenzyloxycarbonyl)-Pregabalin.

These compounds serve as substrates for the peptide transporters PEPT1 and PEPT2 from both human and rat. Further, in vitro metabolism studies demonstrate that these compounds function as prodrugs of gabapentin or pregabalin respectively, undergoing partial or complete conversion to the parent drug after incubation with tissue extracts or isolated enzymes found in gastric fluid or plasma, as described in detail in the Experimental section.

In a preferred embodiment, the compound of Formula (I) is sufficiently stable such that less than 50% of the compound is metabolized after incubation in vitro with Caco-2 homogenate for 1 hour, as described in more detail in Example 6.

Preferred compounds of Formula (I) are prodrugs of GABA analogs that are absorbed from the gastrointestinal tract in mammals by interaction with intestinal peptide transporters. It is particularly preferred that these GABA analog prodrugs be sufficiently stable within the intestinal lumen to be absorbed intact into the systemic circulation, but then undergo efficient conversion back to the GABA analog. This provides a method for achieving better dose-proportional drug exposure than can be attained by oral administration of the parent GABA analog itself, since the PEPT transport pathway is less susceptible to saturation (at high substrate doses) than the large neutral amino acid transport system typically utilized by GABA analogs.

In one preferred embodiment, a compound of Formula (I), upon oral administration to a patient in need of therapy, provides therapeutically efficacious levels of the GABA analog in the plasma of the patient, where the concentration of the GABA analog in plasma of the patient over time provides a curve of concentration of the GABA analog in the plasma over time, the curve having an area under the curve (AUC) which is substantially more proportional to the dose of GABA analog administered, as compared to the proportionality achieved following oral administration of the GABA analog itself. In another preferred embodiment, a compound of Formula (I), upon oral administration to a patient in need of therapy, provides therapeutically efficacious levels of the GABA analog in the plasma of a patient, where the concentration of the GABA analog in plasma of the patient over time provides a curve of concentration of the GABA analog in the plasma over time, the curve having a maximum plasma concentration ($C_{max}$) which is substantially more proportional to the dose of GABA analog administered, as compared to the proportionality achieved following oral administration of the GABA analog itself.

Prodrugs of GABA analogs that are substrates for the peptide transporter PEPT1 are candidates for formulation in sustained release oral dosage forms. Preferred compounds of Formula (I) are prodrugs of GABA analogs that are absorbed from the mammalian colon. Following colonic administration of these prodrugs, the maximum plasma concentrations of the GABA analog, as well as the area under the GABA analog plasma concentration vs. time curves, are significantly greater (>3-fold) than that produced from colonic administration of the GABA analog itself.

Particularly preferred compounds of Formula (I) are compounds selected from the group consisting of L-2-Thienylalanine-Gabapentin, L-4-Methylphenylalanine-Gabapentin, L-4-Trifluoromethylphenylalanine-Gabapentin, L-2-Fluorophenylalanine-Gabapentin, L-4-Fluorophenylalanine-Gabapentin, L-2-Chlorophenylalanine-Gabapentin, L-4-Chlorophenylalanine-Gabapentin, L-4-Bromophenylalanine-Gabapentin, L-4-Iodophenylalanine-Gabapentin, L4-Methoxyphenylalanine-Gabapentin, L-4-Ethoxyphenylalanine-Gabapentin, L-4-Cyanophenylalanine-Gabapentin, L-3,4-Difluorophenylalanine-Gabapentin, D, L-2,4-Difluorophenylalanine-Gabapentin, D, L-2,6-Difluorophenylalanine-Gabapentin, L-2,4-Dichlorophenylalanine-Gabapentin and L-3,4-Dichlorophenylalanine-Gabapentin.

In one aspect, this invention is directed to a pharmaceutical composition comprising a therapeutically effective amount of a compound of Formula (I) and a pharmaceutically acceptable carrier. The pharmaceutical composition may be used to treat or prevent epilepsy, depression, anxiety, psychosis, faintness attacks, hypokinesia, cranial disorders, neurodegenerative disorders, panic, pain (especially neuropathic pain, muscular pain or skeletal pain), inflammatory disease, insomnia, gastrointestinal disorders or ethanol withdrawal syndrome in a patient.

In another aspect, this invention is directed to sustained release oral dosage forms comprising a therapeutically effective amount of a compound of Formula (I) and, optionally, a pharmaceutically acceptable carrier. In one embodiment, the dosage form comprises an osmotic dosage form. In another embodiment, the dosage form comprises a prodrug-releasing polymer. In another embodiment, the dosage form comprises a prodrug-releasing lipid. In another embodiment, the dosage form comprises a prodrug-releasing wax. In another embodiment, the dosage form comprises tiny timed-release pills. In yet another embodiment, the dosage form comprises prodrug releasing beads. Preferably, the prodrug is released from the dosage form over a period of at least about 6 hours, more preferably at least about 8 hours, and most preferably at least about 12 hours. Further, the dosage form preferably releases from 0 to 20% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours.

In another aspect, this invention is directed to a method for treating or preventing epilepsy, depression, anxiety, psychosis, faintness attacks, hypokinesia, cranial disorders, neurodegenerative disorders, panic, pain (especially neuropathic pain, muscular pain or skeletal pain), inflammatory disease, insomnia, gastrointestinal disorders or ethanol withdrawal syndrome in a patient. The method comprises administering to a patient in need of such therapy a therapeutically effective amount of a compound of Formula (I), optionally with a pharmaceutically acceptable vehicle.

In another aspect, this invention is directed to a method for achieving sustained release of a GABA analog in a patient in need of therapy. The method comprises orally administering to the patient a sustained release dosage form containing a therapeutically effective amount of a compound of Formula (I), and optionally, a pharmaceutically acceptable vehicle.

In yet another aspect, this invention is directed to a method for achieving improved dose-proportional exposure of a GABA analog in a patient, said method comprising orally administering to the patient a therapeutically effective amount of a compound of Formula (I) and, optionally, a pharmaceutically acceptable vehicle.

Compound Preparation

Figure 2:
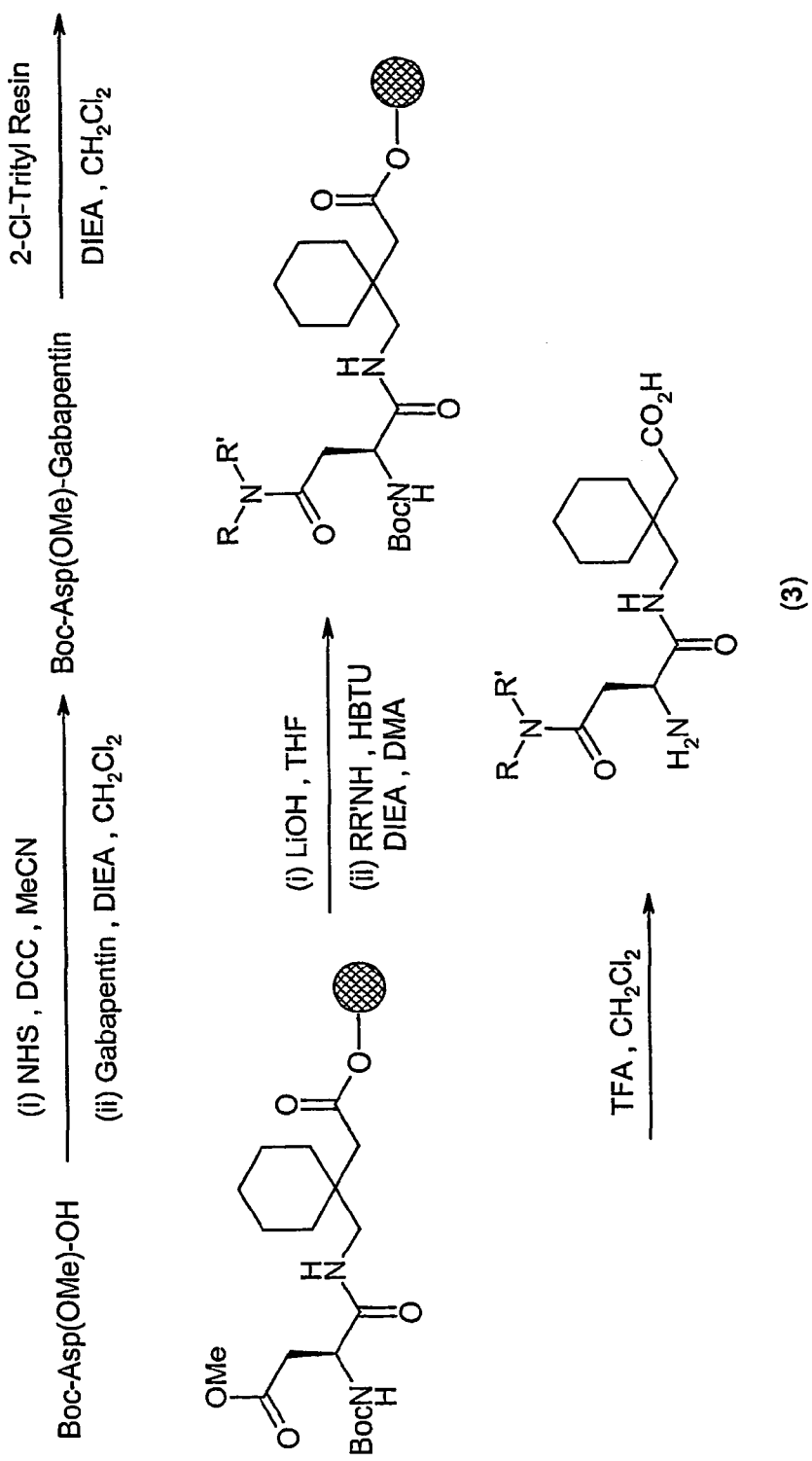
FIG. 2 illustrates the synthesis of L-Aspartyl-Gabapentin derivatives.
Figure 3:
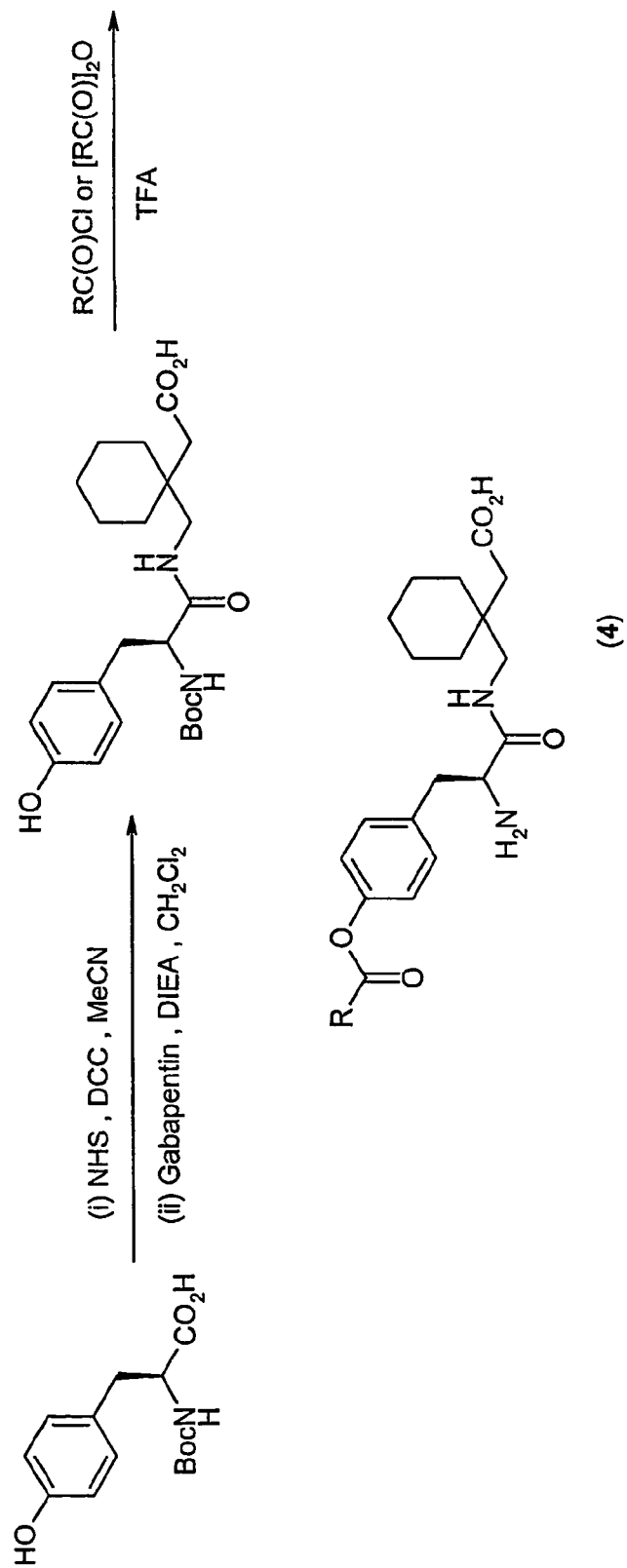
FIG. 3 illustrates the synthesis of L-Tyrosine-Gabapentin derivatives.

Compounds of this invention can be made by various methods, including those illustrated in FIGS. 1-3 and the working examples provided below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1-15 (John Wiley and Sons, 1991); Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Pharmaceutical Formulations

When employed as pharmaceuticals, the compounds of Formula (I) are usually administered in the form of pharmaceutical compositions. These compounds can be administered by a variety of routes including oral, rectal, subcutaneous, intravenous, intramuscular and intranasal. Oral administration of these compounds and compositions is particularly preferred. Such compositions are prepared in a manner well known in the pharmaceutical art and comprise at least one active compound.

This invention also includes pharmaceutical compositions which contain, as the active ingredient, one or more of the compounds of Formula (I) above associated with pharmaceutically acceptable carriers. In making the compositions of this invention, the active ingredient is usually mixed with an excipient, diluted by an excipient or enclosed within such a carrier, which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 to about 5000 mg, more usually about 10 to about 2000 mg, of the active ingredient. The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The present compounds and/or compositions of the invention, which comprise one or more compounds of the invention, are preferably administered orally. In particularly preferred embodiments, the compounds of the invention may be delivered via sustained release systems, preferably oral sustained release systems. Sustained release dosage forms for oral administration are described in greater detail below.

Sustained Release Oral Dosage Forms of the Invention

The present invention can be practiced with a number of different dosage forms, which may be adapted to provide sustained release of the prodrug upon oral administration.

In one embodiment of the invention, the dosage form comprises beads that on dissolution or diffusion release the prodrug over an extended period of hours, preferably, over a period of at least 6 hours, more preferably, over a period of at least 8 hours and most preferably, over a period of at least 12 hours. The prodrug-releasing beads may have a central composition or core comprising a prodrug and pharmaceutically acceptable vehicles, including an optional lubricant, antioxidant and buffer. The beads may be medical preparations with a diameter of about 1 to 2 mm. Individual beads may comprise doses of the prodrug, for example, doses of up to about 40 mg of prodrug. The beads, in one embodiment, are formed of non-cross-linked materials to enhance their discharge from the gastrointestinal tract. The beads may be coated with a release rate-controlling polymer that gives a timed release profile.

The time release beads may be manufactured into a tablet for therapeutically effective prodrug administration. The beads can be made into matrix tablets by the direct compression of a plurality of beads coated with, for example, an acrylic resin and blended with excipients such as hydroxypropylmethyl cellulose. The manufacture of beads has been disclosed in the art (Lu, Int. J. Pharm., 1994, 112, 117-124; Pharmaceutical Sciences by Remington, 14th ed, pp1626-1628 (1970); Fincher, J. Pharm. Sci. 1968, 57, 1825-1835 ( ); and U.S. Pat. No. 4,083,949) as has the manufacture of tablets (Pharmaceutical Sciences, by Remington, 17th Ed, Ch. 90, pp1603-1625 (1985).

In another embodiment, an oral sustained release pump may be used (see Langer, supra; Sefton, 1987, CRC Crit Ref Biomed Eng. 14:201; Saudek et al., 1989, N. Engl. J Med. 321:574).

In another embodiment, polymeric materials can be used (see "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, N.Y. (1984); Ranger and Peppas, 1983, J Macromol. Sci. Rev. Macromol Chem. 23:61; see also Levy et al., 1985, Science 228: 190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, Int. J. Pharm. Tech. & Prod. Mfr., 1984, 5(3) 1-9). Factors affecting drug release are well known to the skilled artisan and have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet another embodiment, drug-releasing lipid matrices can be used for oral sustained release administration. One particularly preferred example is when solid microparticles of the prodrug are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet another embodiment, prodrug-releasing waxes can be used for oral sustained release administration. Examples of suitable sustained prodrug-releasing waxes are disclosed in Cain et al., U.S. Pat. No. 3,402,240 (carnauba wax, candedilla wax, esparto wax and ouricury wax); Shtohryn et al. U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still another embodiment, osmotic delivery systems are used for oral sustained release administration (Verma et al., Drug Dev. Ind. Pharm., 2000, 26:695-708). In a preferred embodiment, OROSâ systems made by Alza Corporation, Mountain View, CA are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the prodrug of the GABA analog, thus requiring only a fraction of the systemic dose (see, e.g., Goodson, in "Medical Applications of Controlled Release," supra, vol. 2, pp. 115-138 (1984)). Other controlled-release systems discussed in Langer, 1990, Science 249:1527-1533 may also be used.

In another embodiment of the invention, the dosage form comprises a prodrug of a GABA analog coated on a polymer substrate. The polymer can be an erodible, or a nonerodible polymer. The coated substrate may be folded onto itself to provide a bilayer polymer drug dosage form. For example prodrug of a GABA analog can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the prodrug over a sustained release period. Representative biodegradable polymer comprise a member selected from the group consisting of biodegradable poly(amides), poly(amino acids), poly(esters), poly (lactic acid), poly(glycolic acid), poly(carbohydrate), poly (orthoester), poly (orthocarbonate), poly(acetyl), poly (anhydrides), biodegradable poly(dehydropyrans), and poly (dioxinones) which are known in the art (Rosoff, Controlled Release of Drugs, Chap. 2, pp. 53-95 (1989); and in U.S. Pat. Nos. 3,811,444; 3,962,414; 4,066,747, 4,070,347; 4,079,038; and 4,093,709).

In another embodiment of the invention, the dosage form comprises a prodrug loaded into a polymer that releases the prodrug by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of a prodrug. The dosage form may be manufactured by procedures known in the art. An example of providing a dosage form comprises blending a pharmaceutically acceptable carrier like polyethylene glycol, with a known dose of prodrug at an elevated temperature, like 37° C., and adding it to a silastic medical grade elastomer with a cross-linking agent, for example, octanoate, followed by casting in a mold. The step is repeated for each optional successive layer. The system is allowed to set for 1 hour, to provide the dosage form. Representative polymers for manufacturing the dosage form comprise a member selected from the group consisting of olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, poly alginate, polyamide and polysilicon. The polymers and procedures for manufacturing them have been described in the art (Coleman et al., Polymers 1990,31, 1187-1231; Roerdink et al., Drug Carrier Systems 1989, 9, 57-10.; Leong et al., Adv. Drug Delivery Rev. 1987, 1, 199-233; Roff et al., Handbook of Common Polymers 1971, CRC Press; U.S. Pat. No. 3,992,518).

In another embodiment of the invention, the dosage from comprises a plurality of tiny pills. The tiny time-released pills provide a number of individual doses for providing various time doses for achieving a sustained-release prodrug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matric comprises a plurality of 4 to 50 tiny pills, each tiny pill comprise a dose population of from 10 ng, 0.5 mg, 1 mg, 1.2 mg, 1.4 mg, 1.6 mg, 5.0 mg etc. The tiny pills comprise a release rate-controlling wall of 0.001 up to 10 mm thickness to provide for the timed release of prodrug. Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in U.S. Pat. Nos. 4,434,153; 4,721,613; 4,853,229; 2,996,431; 3,139,383 and 4,752,470.

In another embodiment of the invention, the dosage form comprises an osmotic dosage form, which comprises a semipermeable wall that surrounds a therapeutic composition comprising the prodrug. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained prodrug release. These delivery platforms can provide an essentially zero order delivery profile as opposed to the spiked profiles of immediate release formulations.

In another embodiment of the invention, the dosage form comprises another osmotic dosage form comprising a wall surrounding a compartment, the wall comprising a semipermeable polymeric composition permeable to the passage of fluid and substantially impermeable to the passage of prodrug present in the compartment, a prodrug-containing layer composition in the compartment, a hydrogel push layer composition in the compartment comprising an osmotic formulation for imbibing and absorbing fluid for expanding in size for pushing the prodrug composition layer from the dosage form, and at least one passageway in the wall for releasing the prodrug composition. The method delivers the prodrug by imbibing fluid through the semipermeable wall at a fluid imbibing rate determined by the permeability of the semipermeable wall and the osmotic pressure across the semipermeable wall causing the push layer to expand, thereby delivering the prodrug from the dosage form through the exit passageway to a patient over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propyl-hyd roxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall comprises a composition that is permeable to the passage of fluid and impermeable to the passage of prodrug. The wall is nontoxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkycellulose such as hydroxypropylmethylcellulose. The total weight percent of all components comprising the wall is equal to 100 wt %. The internal compartment comprises the prodrug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form provided by the invention delivers prodrug from the dosage form to the patient at a zero order rate of release over a period of up to about 24 hours.

The expression "passageway" as used herein comprises means and methods suitable for the metered release of the prodrug from the compartment of the dosage form. The exit means comprises at least one passageway, including orifice, bore, aperture, pore, porous element, hollow fiber, capillary tube, channel, porous overlay, or porous element that provides for the osmotic controlled release of prodrug. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

Regardless of the specific form of sustained release oral dosage form used, the prodrug is preferably released from the dosage form over a period of at least about 6 hours, more preferably, over a period of at least about 8 hours, and most preferably, over a period of at least about 12 hours. Further, the dosage form preferably releases from 0 to 20% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours. The sustained release oral dosage form further provides a concentration of the GABA analog in the blood plasma of the patient over time, which curve has an area under the curve (AUC) that is proportional to the dose of the prodrug of GABA analog administered, and a maximum concentration Cmax. The Cmax is less than 75%, and is preferably, less than 60%, of the Cmax obtained from administering an equivalent dose of the prodrug from an immediate release oral dosage form, and the AUC is substantially the same as the AUC obtained from administering an equivalent dose of the prodrug from an immediate release oral dosage form.

Preferably, the dosage forms of the invention are administered twice per day (more preferably, once per day).

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Cbz = | carbobenzyloxy |
| CPM = | counts per minute |
| DCC = | dicyclohexylcarbodiimide |
| DMAP = | 4-N,N-dimethylaminopyridine |
| DMF = | N,N-dimethylformamide |
| DMSO = | dimethylsulfoxide |
| Fmoc = | 9-fluorenylmethyloxycarbonyl |
| g = | gram |
| h = | hour |
| HBSS = | Hank's buffered saline solution |
| HBTU = | O-Benzotriazolyl tetra-N-methyl-uronium hexafluorophosphate |
| L = | liter |
| LC/MS = | liquid chromatography/mass spectroscopy |

| | |
|---|---|
| M = | molar |
| min = | minute |
| mL = | milliliter |
| mmol = | millimoles |
| NADPH = | nicotinamide-adenine dinucleotide phosphate |
| NHS = | N-hydroxysuccinimide |
| THF = | tetrahydrofuran |
| TFA = | trifluoroacetic acid |
| TMS = | trimethylsilyl |
| μL = | microliter |
| μM = | micromolar |
| v/v = | volume to volume |

Experimental Methods

Example 1

Preparation of Aminoacyl-Gabapentin Derivatives—Method 1

To a 40 mL vial was added an N-Boc-protected amino acid (5 mmol), dicyclohexylcarbodiimide (1.24 g, 6 mmol), N-hydroxysuccinimide (0.7 g, 6 mmol), and acetonitrile (20 mL). The reaction mixture was shaken at 22-25° C. for 4 h. The precipitated dicyclohexylurea was removed by filtration. To the filtrate was added an aqueous solution (30 mL) of gabapentin hydrochloride (1.04 g, 6 mmol), and sodium hydroxide (0.4 g, 10 mmol). The reaction was stirred at 22-25 C for 16 h. The reaction mixture was diluted with ethyl acetate (100 mL) and washed with 0.5 M aqueous citric acid (2×100 mL) and water (2×100 mL). The organic phase was separated, dried (MgSO$_4$), filtered and concentrated under reduced pressure. The residue was dissolved in trifluoroacetic acid (40 mL) and allowed to stand at 22-25° C. for 2 h. The solvent was removed under reduced pressure. The residue was dissolved in water (4 mL) and filtered through a 0.25 μm nylon membrane filter prior to purification by preparative HPLC (Phenomenex 250×21.2 mm, 5 μm LUNA C18 column, 100% water for 5 minutes, then 0-60% acetonitrile in water with 0.05% TFA over 20 minutes at 20 mL/min). The pure fractions were combined and the solvent was removed under reduced pressure to afford the product (1) (typically 70-90%) as a white solid.

The following compounds were prepared according to the method described above:

β-Alanine-Gabapentin (1a): MS (ESI) m/z 241.23 (M−H$^−$), 243.26 (M+H$^+$).

α-Aminoisobutyryl-Gabapentin (1b): MS (ESI) m/z 255.26 (M−H$^−$), 257.28 (M+H$^+$).

D-Alanine-Gabapentin (1c): MS (ESI) m/z 241.24 (M−H$^{31}$), 243.27 (M+H$^+$).

N-Methyl-Glycine-Gabapentin (1d): MS (ESI) m/z 241.24 (M−H$^−$), 243.28 (M+H$^+$).

N-Methyl-L-Valine-Gabapentin (1e): MS (ESI) m/z 283.42 (M−H$^−$), 285.34 (M+H$^+$).

N-Methyl-L-Serine-Gabapentin (1f): MS (ESI) m/z 271.38 (M−H$^−$), 273.41 (M+H$^+$).

N-Methyl-L-Alanine-Gabapentin (1g): MS (ESI) m/z 255.29 (M−H$^−$), 257.29 (M+H$^+$).

L-Pipecolyl-Gabapentin (1h): MS (ESI) m/z 281.23 (M−H$^−$), 283.15 (M+H$^+$).

L-tert-Butylglycine-Gabapentin (1i): MS (ESI) m/z 283.42 (M−H$^−$), 285.2 (M+H$^+$).

L-2,3-Diaminopropionyl-Gabapentin (1j): MS (ESI) m/z 256.3 (M−H$^−$), 258.3 (M+H$^+$).

L-Norvaline-Gabapentin (1k): MS (ESI) m/z 269.2 (M−H$^−$), 271.24 (M+H$^+$).

L-1-Naphthylalanine-Gabapentin (1l): MS (ESI) m/z 367.2 (M−H$^−$), 369.21 (M+H$^+$).

L-2-Naphthylalanine-Gabapentin (1m): MS (ESI) m/z 367.23 (M−H$^−$), 369.3 (M+H$^+$).

L-2-Quinoylalanine-Gabapentin (1n): MS (ESI) m/z 368.18 (M−H$^−$), 370.28 (M+H$^+$).

L-(2-Quinoylalanine N-Oxide)-Gabapentin (1o): MS (ESI) m/z 384.25 (M−H$^−$), 386.87 (M+H$^+$).

L-2-Pyridylalanine-Gabapentin (1p): MS (ESI) m/z 318.23 (M−H$^−$), 320.2 (M+H$^+$).

L-3-Pyridylalanine-Gabapentin (1q): MS (ESI) m/z 318.21 (M−H$^−$), 320.15 (M+H$^+$).

L-(4-Pyridylalanine N-Oxide)-Gabapentin (1r): MS (ESI) m/z 334.24 (M−H$^−$), 336.24 (M+H$^+$).

L-2-Thienylalanine-Gabapentin (1s): MS (ESI) m/z 323.24 (M−H$^−$).

L-3-Thienylalanine-Gabapentin (1t): MS (ESI) m/z 323.24 (M−H$^−$), 325.37 (M+H$^+$).

L-3-Benzothienylalanine-Gabapentin (1u): MS (ESI) m/z 373.26 (M−H$^−$).

L-4-Thiazolylalanine-Gabapentin (1v): MS (ESI) m/z 324.25 (M−H$^−$).

L-2-Methylphenylalanine-Gabapentin (1w): MS (ESI) m/z 331.28 (M−H$^−$), 333.6 (M+H$^+$).

L-4-Methylphenylalanine-Gabapentin (1x): MS (ESI) m/z 331.3 (M−H$^−$).

L-2-Trifluoromethylphenylalanine-Gabapentin (1y): MS (ESI) m/z 385.28 (M−H$^−$), 387.61 (M+H$^+$).

L-3-Trifluoromethylphenylalanine-Gabapentin (1z): MS (ESI) m/z 385.23 (M−H$^−$), 387.63 (M+H$^+$).

L-4-Trifluoromethylphenylalanine-Gabapentin (1aa): MS (ESI) m/z 385.26 (M−H$^−$).

L-2-Fluorophenylalanine-Gabapentin (1ab): MS (ESI) m/z 335.2 (M−H$^−$), 337.19 (M+H$^+$).

L-3-Fluorophenylalanine-Gabapentin (1ac): MS (ESI) m/z 335.19 (M−H$^−$), 337.15 (+H$^+$).

L-4-Fluorophenylalanine-Gabapentin (1ad): MS (ESI) m/z 335.16 (M−H$^−$), 337.21 (M+H$^+$).

L-2-Chlorophenylalanine-Gabapentin (1ae): MS (ESI) m/z 351.14 (M−H$^−$), 353.1 (M+H$^+$).

L-3-Chlorophenylalanine-Gabapentin (1af): MS (ESI) m/z 351.16 (M−H$^−$), 353.08 (M+H$^+$).

L-4-Chlorophenylalanine-Gabapentin (1ag): MS (ESI) m/z 351.15 (M−H$^−$), 353.1 (M+H$^+$).

L-4-Bromophenylalanine-Gabapentin (1ah): MS (ESI) m/z 395.06, 397.05 (M−H$^−$), 397.02, 399.01 (M+H$^+$).

L-4-Iodophenylalanine-Gabapentin (1ai): MS (ESI) m/z 443.01 (M−H$^−$), 445.16 (M+H$^+$).

L-2-Methoxyphenylalanine-Gabapentin (1aj): MS (ESI) m/z 347.21 (M−H$^−$).

L-4-Methoxyphenylalanine-Gabapentin (1ak): MS (ESI) m/z 347.39 (M−H$^−$), 349.92 (M+H$^+$).

L-3-Cyanophenylalanine-Gabapentin (1al): MS (ESI) m/z 342.18 (M−H$^−$), 344.19 (M+H$^+$).

L-4-Cyanophenylalanine-Gabapentin (1am): MS (ESI) m/z 342.2 (M−H$^−$), 344.09 (M+H$^+$).

L-3,4-Difluorophenylalanine-Gabapentin (1an): MS (ESI) m/z 353.12 (M−H$^−$), 355.08 (M+H$^+$).

L-3,5-Difluorophenylalanine-Gabapentin (1ao): MS (ESI) m/z 353.17 (M−H$^−$), 355.18 (M+H$^+$).

D, L-2,4-Difluorophenylalanine-Gabapentin (1ap): MS (ESI) m/z 353.14 (M−H$^−$).

D, L-2,6-Difluorophenylalanine-Gabapentin (1aq): MS (ESI) m/z 353.18 (M−H$^−$), 355.32 (M+H$^+$).

L-2,4-Dichlorophenylalanine-Gabapentin (1ar): MS (ESI) m/z 385.26, 387.03 (M−H⁻), 387.47, 389.08 (M+H⁺).

L-3,4-Dichlorophenylalanine-Gabapentin (1as): MS (ESI) m/z 385.1, 387.03 (M−H⁻), 387.07, 388.99 (M+H⁺).

L-Penicillamine-Gabapentin (1at): MS (ESI) m/z 301.18 (M−H⁻), 303.14 (M+H⁺).

1-Aminocyclopropane-1-Carbonyl-Gabapentin (1au): MS (ESI) m/z 253.23 (M−H⁻), 255.2 (M+H⁺).

1-Aminocyclohexane-1-Carbonyl-Gabapentin (1av): MS (ESI) m/z 295.24 (M−H⁻), 297.25 (N+H⁺).

L-Homophenylalanine-Gabapentin (1aw): MS (ESI) m/z 331.15 (M−H⁻).

L-Serine-Gabapentin (1ax): MS (ESI) m/z 257.11 (M−H⁻), 259.10 (M+H⁺).

Preparation of Aminoacyl-Gabapentin Derivatives—Method 2

To an ice-cold reaction mixture containing an N-Boc-protected amino acid (1 mmol) and triethylamine (0.278 mL, 2 mmol) in anhydrous THF (100 mL) was added ethyl chloroformate (0.115 mL, 1.2 mmol). The reaction mixture was stirred at 0° C. for 30 min. A solution of gabapentin hydrochloride salt (311 mg, 1.5 mmol) in 0.5 N NaOH (6 mL) was added at 0° C., stirred for 30 min at 0° C. and then 30 min at room temperature. After evaporation of the THF under reduced pressure, saturated citric acid (20 mL) was added. The product was extracted with ethyl acetate (3×30 mL) and the combined organic phase dried over MgSO₄ and concentrated to dryness. The resulting residue was treated with 80% (v/v) TFA in dichloromethane at room temperature for 30 min. The reaction mixture was evaporated to dryness. The aminoacyl-Gabapentin product was purified by preparative HPLC as described above.

Example 2

Preparation of Aspartyl-Gabapentin Derivatives

To a solution of Boc-Asp(OMe)-OH (5 g, 20 mmol) in acetonitrile (100 mL) was added N-hydroxysuccinimide (2.53 g, 22 mmol) and N,N-dicyclohexylcarbodiimide (4.5 g, 22 mmol). The reaction was stirred at ambient temperature for 4 h. The reaction mixture was filtered directly into an aqueous solution (100 mL) of gabapentin (3.77 g, 22 mmol) and sodium hydrogencarbonate (1.85 g, 22 mmol) and the resulting mixture stirred at ambient temperature for 16 h. The reaction was concentrated under reduced pressure, the residue dissolved in ethyl acetate/diethyl ether (1:1, 300 mL) and washed with 0.1M aqueous potassium hydrogensulfate (2×500 mL). The organic phase was separated, dried over Na₂SO₄, filtered, and concentrated to dryness under reduced pressure to afford Boc-Asp(OMe)-Gabapentin as a white solid (7.8 g, 19.5 mmol, 98%).

To 250 mL peptide vessel was added 2-chlorotritylchloride resin (10 g, 1.69 mmol/g, 16.9 mmol), and a solution of Boc-Asp(OMe)-Gabapentin (7.8 g, 19.5 mmol) in dichloromethane (125 mL). N,N-Diisopropylethylamine (5.2 mL, 30 mmol) was added and the vessel was shaken at ambient temperature for 1 h. The resin was drained and washed consecutively with dichloromethane (3×250 mL), methanol (3×250 mL), and tetrahydrofuran (3×250 mL). The resin was shaken with lithium hydroxide (0.5 g) in tetrahydrofuran (100 mL), water (10 mL), and methanol (25 mL) at ambient temperature for 2 h. The resin was drained and washed with methanol (3×250 mL), dichloromethane (3×250 mL), and N,N-dimethylformide (3×250 mL). The resin was aliquoted into 10 100 mL Alltech tubes and a solution of HBTU (32 g, 84 mmol) in N,N-dimethylacetamide (250 mL) and N,N-diisopropylethylamine (22 mL) was distributed evenly to each vessel.

To each of the ten vessels was added 5 equivalents of one of the following 10 amines: (a) pyrrolidine; (b) butylamine; (c) 2-methoxyethylamine; (d) piperidine; (e) isoamylamine; (f) cyclohexylamine; (g) 4-aminomethylpyridine; (h) 3-aminomethylpyridine; (i) heptylamine; and () 3,4-dimethoxyphenethyl-amine. The vessels were capped and shaken at ambient temperature for 16 h. The resins were drained and washed with 1-methylpyrrolidinone (3×100 mL), methanol (3×100 mL), and dichloromethane (3×100 mL). The resins were each treated with 25% trifluoroacetic acid in dichloromethane (20 mL) for 10 minutes, and drained into 40 mL vials. The solvent was removed under reduced pressure. The residues were dissolved in acetonitrile/water (1:1, 5 mL) and filtered through a 0.2 μm nylon membrane filter. The solutions were purified by preparative HPLC. The pure fractions were combined and concentrated under reduced pressure. The pure compounds were redissolved in 20% acetonitrile in water (10 mL), frozen, and lyophilized to afford 15-30 mg of each of the following compounds as white powders:

L-Aspartyl-β-(Pyrrolidinyl)-Gabapentin (3a): MS (ESI) m/z 338.28 (M−H⁻), 340.29 (M+H⁺).

L-Aspartyl-β-(Butylamido)-Gabapentin (3b): MS (ESI) m/z 340.31 (M−H⁻), 342.32 (M+H⁺).

L-Aspartyl-β-(2-Methoxyethylamido)-Gabapentin (3c): MS (ESI) m/z 342.30 (M−H⁻), 344.29 (M+H⁺).

L-Aspartyl-β-(Piperidinyl)-Gabapentin (3d): MS (ESI) m/z 352.32 (M−H⁻), 354.31 (M+H⁺).

L-Aspartyl-β-(3-Methylbutylamido)-Gabapentin (3e): MS (ESI) m/z 354.32 (M−H⁻), 356.37 (M+H⁺).

L-Aspartyl-β-(Cyclohexylamido)-Gabapentin (3f): MS (ESI) m/z 366.33 (M−H⁻), 368.32 (M+H⁺).

L-Aspartyl-β-(4-Amidomethylpyridine)-Gabapentin (3g): MS (ESI) m/z 375.27 (M−H⁻), 377.29 (M+H⁺).

L-Aspartyl-β-(3-Amidomethylpyridine)-Gabapentin (3h): MS (ESI) m/z 375.25 (M−H⁻), 377.25 (M+H⁺).

L-Aspartyl-β-(Heptylamido)-Gabapentin (3i): MS (ESI) m/z 382.32 (M−H⁻), 384.42 (M+H⁺).

L-Aspartyl-β-(3,4-Dimethoxyphenethylamido)-Gabapentin (3j): MS (ESI) m/z 448.23 (M−H⁻), 450.27 (M+H⁺).

L-Aspartyl-β-(O-Cyclohexyl ester)-Gabapentin (3k)

To a solution of L-Boc-Aspartyl-β-(O-Cyclohexyl ester)-OH (1 g, 3.2 mmol) in acetonitrile (20 mL) was added N-hydroxysuccinamide (391 mg, 3.4 mmol), and N,N-dicyclohexylcarbodiimide (702 mg, 3.4 mmol). The reaction was shaken at ambient temperature for 4 h. The reaction was filtered directly into an aqueous solution (100 mL) of gabapentin (582 mg, 3.4 mmol) and sodium hydrogencarbonate (286 mg, 3.4 mmol) and the resulting mixture was shaken at ambient temperature for 16 h. The reaction was diluted with ethyl acetate/diethyl ether (1:1, 100 mL) and washed with 0.1M aqueous potassium hydrogensulfate (2×150 mL). The organic phase was separated, dried over Na₂SO₄, filtered, and concentrated to dryness under reduced pressure to afford the L-Boc-Aspartyl-β-(O-Cyclohexyl ester)-Gabapentin as a white solid. The compound was dissolved in 33% trifluoroacetic acid in dichloromethane (100 mL) and stirred at ambient temperature for 1 h. The solvent was removed under reduced pressure. The residue was dissolved in acetonitrile/water (1:1, 10 mL) and filtered through a 0.2 μm nylon membrane filter. The solution was purified by preparative HPLC. The pure fractions were combined and concentrated under reduced pressure to afford the title compound (3k) as a white powder. MS (ESI) m/z 367.39 (M−H⁻), 369.81 (M+H⁺).

L-Aspartyl-β-(O-Benzyl ester)-Gabapentin (3l)

To a solution of L-Boc-Aspartyl-β-(O-Benzyl ester)-OH (1 g, 3.2 mmol) in acetonitrile (20 mL) was added N-hydroxysuccinamide (391 mg, 3.4 mmol), and N,N-dicyclohexylcarbodiimide (702 mg, 3.4 mmol). The reaction was shaken at ambient temperature for 4 h. The reaction was filtered directly into an aqueous solution (100 mL) of gabapentin (582 mg, 3.4 mmol) and sodium hydrogencarbonate (286 mg, 3.4 mmol) and the resulting mixture was shaken at ambient temperature for 16 h. The reaction was diluted with ethyl acetate/diethyl ether (1:1, 100 mL) and washed with 0.1M aqueous potassium hydrogensulfate (2×150 mL). The organic phase was separated, dried over $Na_2SO_4$, filtered, and concentrated to dryness under reduced pressure to afford the L-Boc-Aspartyl-β-(O-Benzyl ester)-Gabapentin as a white solid. The compound was dissolved in 33% trifluoroacetic acid in dichloromethane (100 mL) and stirred at ambient temperature for 1 h. The solvent was removed under reduced pressure. The residue was dissolved in acetonitrile/water (1:1, 10 mL) and filtered through a 0.2 µm nylon membrane filter. The solution was purified by preparative BPLC. The pure fractions were combined and concentrated under reduced pressure to afford the title compound (3l) as a white powder. MS (ESI) m/z 375.28 (M−H⁻), 377.65 (M+H⁺).

Example 3

Preparation of Tyrosine-Gabapentin Derivatives

To a solution of Boc-Tyr-OH (4.2 g, 15 mmol) in acetonitrile (100 mL) was added N-hydroxysuccinamide (1.84 g, 16 mmol) and N,N-dicyclohexylcarbodiimide (3.3 g, 16 mmol). The reaction was stirred at ambient temperature for 2 h. The reaction mixture was filtered directly into an aqueous solution (100 mL) of gabapentin (2.7 g, 16 mmol) and sodium hydroxide (640 mg, 16 mmol), and the resulting mixture stirred at ambient temperature for 16 h. The reaction was concentrated under reduced pressure, the residue was dissolved in ethyl acetate/diethyl ether (1/1, 200 mL) and washed with 0.1M aqueous potassium hydrogensulfate (2×200 mL). The organic phase was separated, dried over $Na_2SO_4$, filtered, and concentrated to dryness under reduced pressure to afford Boc-Tyr-Gabapentin as a white solid (7.4 g, 16 mmol).

Boc-Tyr-Gabapentin (434 mg, 1 mmol) was treated with trifluoroacetic acid (10 mL) at ambient temperature for 1 h, followed by the addition of an acid chloride, symmetrical anhydride or chloroformate (0.9 mmol). The reactions were stirred at ambient temperature for 1 h. The solvent was removed under reduced pressure and the residues dissolved in acetonitrile/water (1:1, 5 mL) and filtered through a 0.2 µm nylon membrane filter. The solutions were purified by preparative HPLC. The pure fractions were combined and concentrated under reduced pressure to afford each of the following compounds as colorless syrups:

L-Tyrosine-(O-2,6-Dimethylbenzoyl)-Gabapentin (4a): MS (ESI) m/z 465.33 (M−H⁻), 467.33 (M+H⁺).

L-Tyrosine-(O-2,6-Dimethoxybenzoyl)-Gabapentin (4b): MS (ESI) m/z 497.34 (M−H⁻), 499.30 (M+H⁺).

L-Tyrosine-(O-2-Methylbenzoyl)-Gabapentin (4c): MS (ESI) m/z 451.31 (M−H⁻), 453.35 (M+H⁺).

L-Tyrosine-(O-2-Bromobenzyloxycarbonyl)-Gabapentin (4d): MS (ESI) m/z 544.12, 546.14 (M−H⁻), 546.15, 548.16 (M+H⁺).

Example 4

Preparation of L-4-Bromophenylalanine-Pregabalin (5)

A suspension of L-Boc-4-bromophenylalanine (500 mg, 1.46 mmol), N-hydroxysuccinimide (173 mg, 1.50 mmol), N,N-dicyclohexylcarbodiimide (310 mg, 1.50 mmol) in acetonitrile was stirred at room temperature for 1 h. Then the reaction mixture was filtered directly into a stirred aqueous solution of pregabalin (239 mg, 1.50 mmol) and NaOH (60 mg, 1.5 mmol). The resulting mixture was stirred for another hour at room temperature. After removing the organic solvent under reduced pressure, the aqueous solution was acidified to pH 3 with $KHSO_4$ and the resulting mixture was extracted with ethyl acetate:ether (1:2). The organic extract was washed with brine and dried over $Na_2SO_4$. After removing the solvent under reduced pressure, the residue was dissolved in 4N HCl in dioxane (10 mL) and stirred at room temperature for 2 h. The solution was concentrated under reduced pressure to afford white precipitate. Re-crystallization from hot water followed by HPLC purification afforded 412 mg of the title compound (5). $^1$H-NMR (CD$_3$OD, 400 MHz): δ 0.86 (d, J=6.8 Hz, 3 H), 0.89 (d, J=6.8 Hz, 3H), 1.06 (m, 2H), 1.64 (m, 1H), 2.08-2.00 (m, 3H), 3.00 (m, 2H), 3.12 (dd, J=14.0, 7.4 Hz, 1H), 3.25 (overlapped with methanol, 1H), 3.95 (m, 1H), 7.19 (d, J=8.0 Hz, 2H), 7.50 (d, J=8 Hz, 2H).

Example 5

In Vitro Compound Transport Assays with PEPT1 and PEPT2-Expressing Cell Lines (a) Inhibition of Radiolabeled Gly-Sar Uptake Rat and human PEPT1 and PEPT2 expressing CHO cell lines were prepared as described in PCT Application WO01/20331. Gabapentin-containing dipeptides were evaluated for interaction with the peptide transporters using a radiolabeled substrate uptake assay in a competitive inhibition format, as described in PCT Application WO01/20331. Transport-induced currents were also measured in *Xenopus* oocytes transfected with rat and human PEPT1 and PEPT2.

(b) Analysis of Electrogenic Transport in *Xenopus* Oocytes

RNA preparation: Rat and human PEPT1 and PEPT2 transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

*Xenopus* oocyte isolation. *Xenopus laevis* frogs were anesthetized by immersion in Tricaine (1.5 g/mL in deionized water) for 15 min. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80-100 min with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10-20 µg RNA in 45 µL solution.

Electrophysiology measurements. Transport currents were measured 2-14 days after injection, using a standard two-electrode electrophysiology set-up (Geneclamp 500 amplifier, Digidata 1320/PCLAMP software and ADInstruments hardware and software were used for signal acquisition). Electrodes (2-4 mΩ) were microfabricated using a Sutter Instrument puller and filled with 3M KCl. The bath was directly grounded (transporter currents were less than 0.3 μA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4-8 Hz. All bath and drug-containing solutions were frog ringers solution containing $CaCl_2$. Drugs were applied for 10-30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to transport rate. Recordings were made from a single oocyte for up to 60 min, enabling 30-40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of glycyl-sarcosine (1 mM) was used as a common reference to normalize results from test compounds. Using this normalization procedure $I_{max}$ (i.e. maximal induced current) for different compounds tested on different oocytes could be compared.

Each of the compounds (1a)-(1ax), (3a)-(3l) and (5) elicited PEPT-specific currents significantly above background (at least 5% of $I_{max}$ for Gly-Sar) when tested at 1 mM on oocytes expressing either PEPT1 or PEPT2, confirming that these compounds serve as substrates for both of these transporters.

Example 6

In Vitro Enzymatic Release of Gabapentin from Aminoacyl-Gabapentin Conjugates

The stability of aminoacyl-gabapentin conjugates was evaluated by incubating the conjugates in the various tissue and enzyme-containing preparations listed in Table 1 below.

Tissue homogenates and plasma samples were obtained from commercial sources (Pel-Freez Biologicals, Rogers, Ark., and GenTest Corporation, Woburn, Mass.). Stability of prodrugs toward the specific enzyme aminopeptidase was also evaluated by incubation with the purified enzyme. Experimental conditions used for the in vitro studies were as follows. Each preparation was incubated with test compound at 37° C. for one hour. Aliquots (50 μL) were removed at 0, 30, and 60 min and quenched with 0.1% trifluoroacetic acid in acetonitrile. Samples were then centrifuged and analyzed for the presence of prodrug and released gabapentin by LC/MS/MS as described below.

Rat intestinal wash is obtained from rats post-morten by rinsing the surgically separated intesting with small volumes (about 3 mL) of buffered saline.

Concentrations of prodrug or gabapentin in tissue extracts were determined by direct injection onto an API 2000 LC/MS/MS equipped with an Agilent 1100 binary pump and autosampler. Separation was achieved using a 3.5 μm Zorbax Ellipse XDB-C8 4.4×150 mm column heated to 45° C. during the analysis. The mobile phases were: 0.1% formic acid in water (A) and 0.1% formic acid in acetonitrile (B). The gradient condition was: 2% B for 0.5 min, increasing to 90% B in 2.0 min, maintained for 2.5 min and returning to 2% B for 2 min. A TurboIonSpray source was used on the API 2000. The analysis was performed in the positive ion mode and MRM transitions of 172.0/137.2 were used in the analysis of gabapentin (2). Ten microliters of the sample extracts were injected. Peaks were integrated using Analyst quantitation software. The method was linear for (2) over the concentration range 0.002 to 2.5 μg/mL respectively.

The stability of gabapentin-containing prodrugs to Caco-2 homogenates was evaluated as follows:

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9000 g for 20 min at 4° C. The resulting supernatant (Caco-2 cell homogenate S9 fraction) was aliquoted into 0.5 mL vials and stored at −80° C. until used.

For stability studies, prodrug (5 μM) was incubated in Caco-2 homogenate S9 fraction (0.5 mg protein per mL) for 60 min at 37° C. Concentrations of intact prodrug and released drug were determined at zero time and 60 minutes using LC/MS/MS.

Aminyopeptidase Stability: Aminopeptidase 1 (Sigma catalog # A-9934) was diluted in deionised water to a concentration of 856 units/mL. Stability studies were conducted by incubating prodrug (5 μM) with 0.856 units/mL aminopeptidase 1 in 50 mM Tris-HCl buffer at pH 8.0 and 37° C. Concentrations of intact prodrug and released drug were determined at zero time and 60 minutes using LC/MS/MS.

TABLE 1

Experimental Conditions for In Vitro Enzymatic Release of Gabapentin in 60 minutes from Aminoacyl-Gabapentin Prodrugs

| Preparation | Substrate Concentration | Cofactors |
|---|---|---|
| Rat Plasma | 2.0 μM | None |
| Human Plasma | 2.0 μM | None |
| Rat Liver S9 (0.5 mg/mL) | 2.0 μM | NADPH |
| Human Liver S9 (0.5 mg/mL) | 2.0 μM | NADPH |
| Human Intestine S9 (0.5 mg/mL) | 2.0 μM | NADPH |
| Rat Intestinal Wash | 5.0 μM | None |
| Caco-2 Homogenate | 5.0 μM | None |
| Aminopeptidase | 5.0 μM | None |

Each of the compounds (1h)-(1aw) showed either partial or complete conversion to gabapentin (2) when treated with either Caco-2 homogenate or aminopeptidase under the conditions described above.

Incubation with Caco-2 homogenate for 1 hour resulted in metabolism of >50% of the following compounds (% of prodrug surviving intact in parenthesis): (1l) (29%); (1al) (46%); (1ao) (48%); (4d) (3%).

Incubation with Caco-2 homogenate for 1 hour resulted in metabolism of <50% of the following compounds (% of prodrug surviving intact in parenthesis): (1aa) (97%); (1ah) (79%); (1am) (90%); (1ap) (90%).

Example 7

Uptake of Gabapentin (2) Following Oral Administration of Prodrugs to Rats

The pharmacokinetics of the prodrugs prepared in Examples 1 and 3 were examined in rats. Three groups of four male Sprague-Dawley rats (approx 200 g) with jugular cannulae each received one of the following treatments: A) a single bolus intravenous injection of gabapentin (25 mg/kg, as a solution in water); B) a single oral dose of gabapentin (25 mg/kg, as a solution in water) administered by oral gavage; C) a single oral dose of prodrug (25 mg-equivalents of gabapentin per kg body weight, as a solution in water) administered by oral gavage. Animals were fasted overnight prior to dosing and until 4 hours post-dosing. Serial blood samples were obtained over 24 hours following dosing and blood was processed for plasma by centrifugation. Plasma samples were stored at −80° C. until analyzed.

Concentrations of prodrug or gabapentin in plasma samples were determined by LC/MS/MS as described above. Plasma (50 µL) was precipitated by addition of 100 mL of methanol and supernatant was injected directly onto the LC/MS/MS system. Following oral administration of gabapentin, concentrations of gabapentin in plasma reached a maximum plasma concentration ($C_{max}$) of 10.3 µg/mL and declined thereafter with a terminal half-life of 2.4±0.5 hours. The oral bioavailability of gabapentin was 87±18%. Following oral administration of gabapentin prodrugs, concentrations of prodrug and gabapentin in plasma were monitored over 24 hours. The $C_{max}$ values for prodrug ($C_{max}$ PD) were as follows:

(1l) $C_{max}$ PD=0.5 µg/mL (1al) $C_{max}$ PD=0.6 µg/mL (1ao) $C_{max}$ PD=2.9 µg/mL (4d) $C_{max}$ PD=<0.004 µg/mL (1aa) $C_{max}$ PD=30.0 µg/mL (1ah) $C_{max}$ PD=103 µg/mL (1am) $C_{max}$ PD=22.4 µg/mL (1ap) $C_{max}$ PD=278 µg/mL This data indicates that gabapentin prodrugs which undergo substantial (i.e >50%) degradation in the presence of enterocyte (Caco-2) homogenate over a period of 1 h in vitro (e.g. (1l), (1al), (1ao) and (4d)) produce low maximal plasma prodrug concentrations following oral administration to rats. This is likely due to presystemic hydrolysis (or other metabolism) of the prodrug, either within the intestinal lumen, at the enterocyte brush-border membrane or intracellularly (within enterocytes lining the GI tract).

The $C_{max}$ value for gabapentin following oral administration of (1ah) was 6.1 µg/mL, and its oral bioavailability (F) as gabapentin was 53%. Prodrugs of gabapentin have an oral bioavailability (F) as gabapentin preferably of at least 40%, more preferably of at least 50%, and most preferably of at least 75%.

Example 8

Uptake of Gabapentin (2) Following Oral Administration of (1ax) to Monkeys and Rats The pharmacokinetics of prodrug (1ax) was examined in adult male cynomologous monkeys. The prodrug was administered orally to four adult male monkeys (approximate body weight of 6.5 kg) via an oral nasogastric tubeas solutions in water or PEG 400. The dose was 10 or 75 mg-equivalents of gabapentin per kg body weight. Animals were fasted overnight before the study and for 4 hours post-dosing. Blood samples (1.0 mL) were obtained via femoral or cephalic venipuncture at intervals over 48 hours after oral dosing. Blood was processed immediately for plasma and plasma was frozen at −80° C. until analyzed. Concentrations of (1ax) or gabapentin (2) in plasma samples were determined by LC/MS/MS as previously described, using MRM transitions of 259.20/154.00 for analysis of (1ax). Oral bioavailability was determined by comparison of area under the gabapentin concentration versus time curve (AUC) following oral administration of prodrug or intravenous administration of an equimolar dose of gabapentin hydrochloride. The $C_{max}$ and AUC values for gabapentin (2) ($C_{max}$ G; AUC G), and the oral bioavailability as gabapentin (F) for each treatment were as follows:

(2) at 10 mg-eq/kg: $C_{max}$ G=3.7±1.6 µg/mL; AUC G=32.1±10.4 µg.h/mL; F=53.9±17.3%.

(1ax) at 10 mg-eq/kg: $C_{max}$ G=3.7±1.1 µg/mL; AUC G=24.7±7.3 µg.h/mL; F=41.5±12.2%.

(2) at 75 mg-eq/kg: $C_{max}$ G=10.8±1.3 µg/mL; AUC G=102±4.9 µg.h/mL; F=22.9±1.1%.

(1ax) at 75 mg-eq/kg: $C_{max}$ G=14.5±1.6 µg/mL; AUC G=125±5.0 µg.h/mL; F=28.1±1.1%.

This data shows a statistically significant increase ($p<0.05$) in both $C_{max}$ and AUC for gabapentin after oral administration as the prodrug (1ax), as compared to dosing of an equimolar amount of gabapentin (2) itself at the high dose (75 mg-eq./kg) level. A 7.5-fold increase in gabapentin dose results in only a 3.2-fold increase in gabapentin exposure (as measured by AUC), while a 7.5-fold increase in prodrug dose results in a 5.1-fold increase in gabapentin exposure (as measured by AUC). Thus the less than dose-proportional increase in gabapentin exposure observed following gabapentin dosing at levels sufficient to saturate the drug's normal uptake pathway can be offset, in part, by administering a prodrug that exploits a higher capacity uptake mechanism (e.g. the PEPT transporter).

However, oral and i.v. dosing of prodrug (1ax) to rats has demonstrated that the fraction of (1ax) absorbed intact following oral administration is only about 15-20%, indicating that the majority of the prodrug is hydrolyzed to gabapentin presystemically (probably within the intestinal lumen). This presystemically generated gabapentin is subject to absorption via the same saturable pathway normally used by gabapentin. This data is consistent with the less than full dose-proportional increase in gabapentin exposure observed following prodrug (1ax) dose acsension in monkeys, since it is likely that only a fraction of the prodrug survived intra-lumenally to take advantage of a higher capacity uptake pathway via the peptide transporter.

In contrast to (1ax), oral and i.v. dosing of prodrug (1ah) to rats has demonstrated that the fraction of (1ah) absorbed intact following oral administration is about 60%, with the prodrug converting rapidly to (2) within the systemic circulation and providing gabapentin with an oral bioavailability of about 53%. Thus the 4-bromophenylalanine-containing gabapentin dipeptide is a more preferred prodrug than the serine compound for exploiting the greater uptake capacity of intestinal peptide transporters.

Example 9

Uptake of Gabapentin (2) Following Oral Administration of (1ah) to Monkeys

The pharmacokinetics of the prodrug (1ah) was examined in adult male cynomologous monkeys. The prodrug was administered as its sodium salt orally to four adult male monkeys (approximate body weight of 6.5 kg) via an oral nasogastric tubeas solutions in water. The dose was 10 mg-equivalents of gabapentin per kg body weight. Animals were fasted overnight before the study and for 4 hours post-dosing. Blood samples (1.0 mL) were obtained via femoral or cephalic venipuncture at intervals over 48 hours after oral dosing. Blood was processed immediately for plasma and plasma was frozen at −80° C. until analyzed. Concentrations of (1ah) and (2) in plasma samples were determined by LC/MS/MS as previously described, using MRM transitions of 399.07/200.02 for analysis of (1ah). Oral bioavailability was determined by comparison of area under the gabapentin concentration versus time curve (AUC) following oral administration of prodrug or intravenous administration of an equimolar dose of gabapentin hydrochloride.

Pharmacokinetic parameters for (1ah) were as follows:

$C_{max\ G}$=3.8±1.1 μg/mL; AUC G=29.1±3.5 μg.h/mL;
  $C_{max}$ PD=14.9±5.3 μg/mL; AUC PD=18.9±6.5
  μg.h/mL; F=49.1±6.8%.

This data corroborates in monkeys the finding from rats that (1ah) is effectively absorbed intact after oral dosing and undergoes rapid conversion to gabapentin.

Example 10

Uptake of Gabapentin Following Administration of Gabapentin or Prodrug (1ah) Intracolonically in Rats Sustained release oral dosage forms, which release drug slowly over periods of 6-24 hours, generally release a significant proportion of the dose within the colon. Thus drugs suitable for use in such dosage forms preferably exhibit good colonic absorption. This experiment was conducted to assess the suitability of a gabapentin prodrug ((1ah)) for use in an oral sustained release dosage form.

Rats were obtained commercially and were pre-cannulated in the both the ascending colon and the jugular vein. Animals were conscious at the time of the experiment. All animals were fasted overnight and until 4 hours post-dosing. Gabapentin or (1ah) (as the sodium salt) were administered as solutions in water directly into the colon via the cannula at a dose equivalent to 25 mg of gabapentin per kg. Blood samples (0.5 mL) were obtained from the jugular cannula at intervals over 8 hours and were quenched immediately by addition of acetonitrile/methanol to prevent further conversion of the prodrug. Blood was processed for plasma by centrifugation and concentrations of prodrug (1ah) or (2) in plasma samples were determined by LC/MS/MS as previously described. Following colonic administration of (1 ah) the maximum plasma concentrations of gabapentin, as well as the area under the gabapentin plasma concentration vs. time curves, were significantly greater (>3-fold) than that produced from colonic administration of gabapentin itself.

This data demonstrates that compounds of the invention may be formulated as compositions suitable for enhanced absorption and/or effective sustained release of GABA analogs to minimize dosing frequency due to rapid systemic clearance of these GABA analogs.

What is claimed is:

1. A compound having the formula:

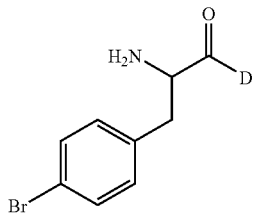

wherein:

D is a moiety selected from the group consisting of the following GABA analog moieties:

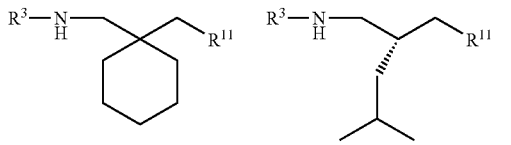

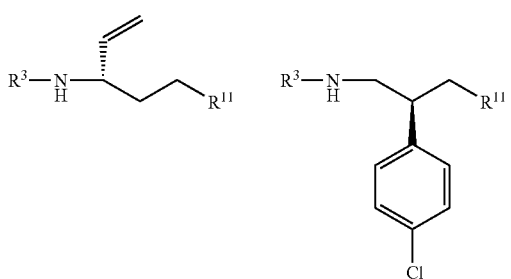

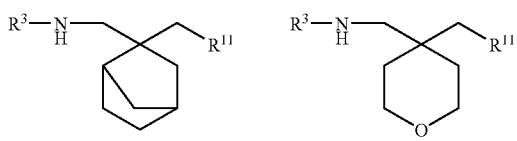

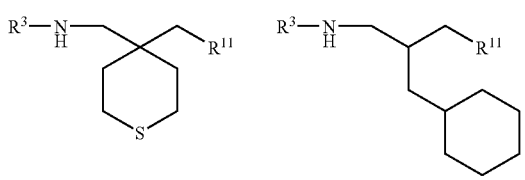

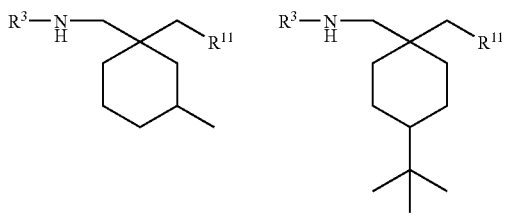

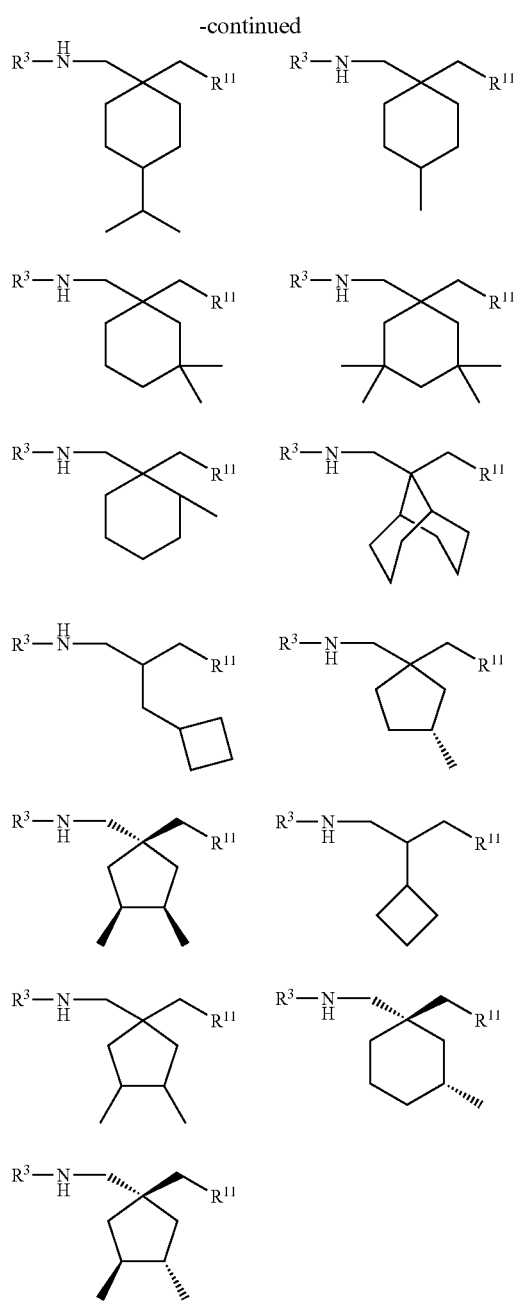
wherein $R^3$ is a covalent bond; and $R^{11}$ is —COOH; and pharmaceutically acceptable salts thereof.
2. A compound having the formula:
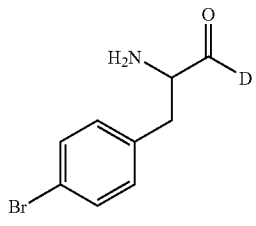
wherein:
D is a moiety selected from the group consisting of the following GABA analog moieties:
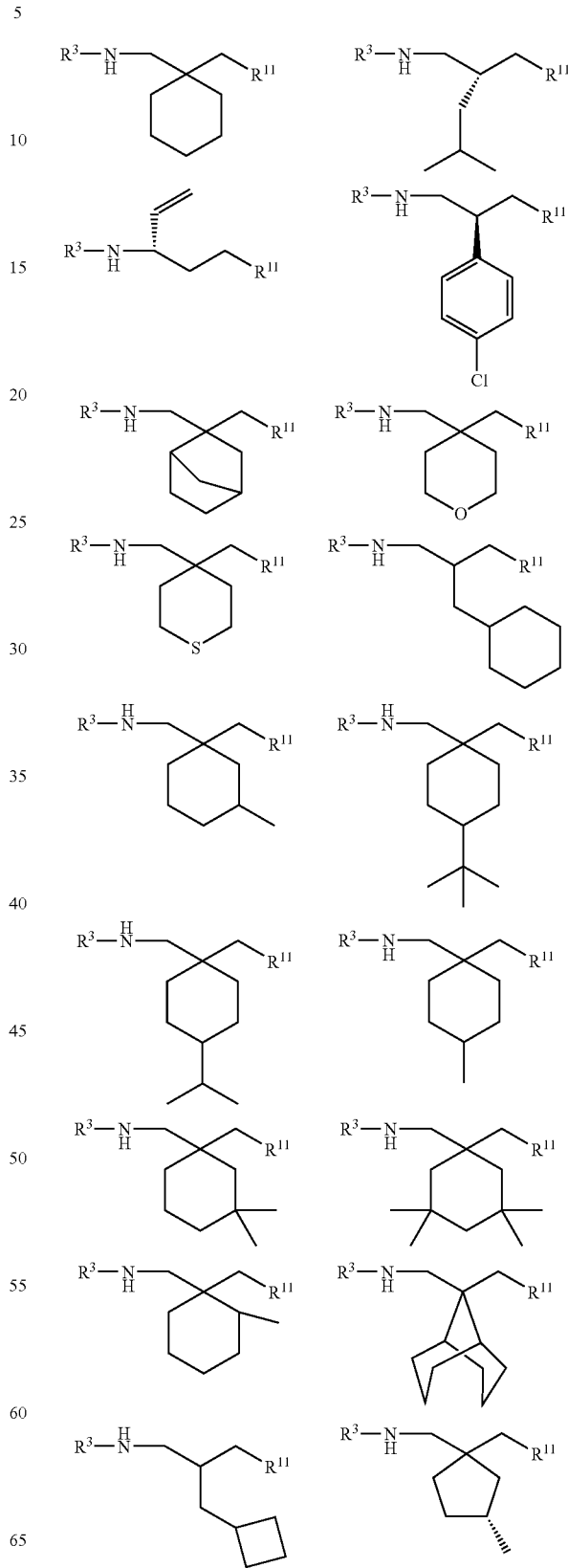

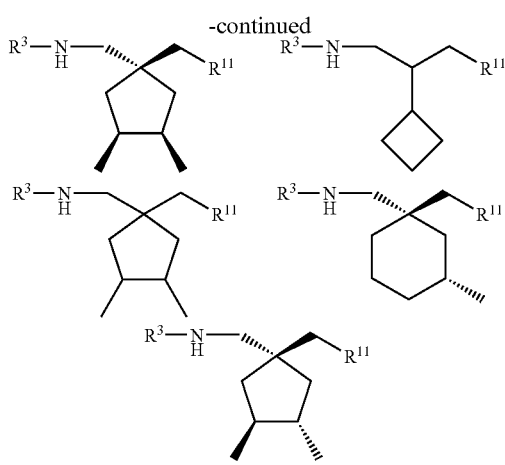

wherein $R^3$ is a covalent bond; and $R^{11}$ is —COOH;

and pharmaceutically acceptable salts thereof;

provided that the compound has a half-life of at least 1 hour when incubated in vitro at 37° C. at a concentration of 5 uM with an S9 fraction of Caco-2 cell homogenate at a protein concentration of 0.5 mg/mL.

3. A compound of claim 1, which upon oral administration to a patient in need of therapy, provides therapeutically efficacious levels of a GABA analog in the plasma of the patient, where the GABA analog in the plasma of the patient has a concentration which over time provides a curve of concentration of the GABA analog in the plasma over time, the curve having an area under the curve (AUC) or a maximum plasma concentration ($C_{max}$) which is substantially more proportional to the dose of GABA analog administered, as compared to the proportionality achieved following oral administration of the GABA analog itself.

4. A compound of claim 1, which is metabolized to produce a GABA analog at a sufficient rate in vivo, upon colonic administration to rats, to produce a $C_{max}$ or an AUC of the GABA analog in plasma of at least 200% of the $C_{max}$ or an AUC of the GABA analog in plasma achieved by colonically administering an equimolar dose of the GABA analog itself.

5. A pharmaceutical composition comprising a therapeutically effective amount of a compound according to claim 1 and a pharmaceutically acceptable carrier.

6. An oral dosage form comprising:
   a sustained release oral dosage form containing a compound of claim 1, the dosage form being adapted for oral delivery to a patient;
   the dosage form further being adapted to release the compound gradually into the intestinal lumen of the patient over a period after oral administration.

7. The dosage form of claim 6, wherein the period comprises at least about 6 hours.

8. The dosage form of claim 6, wherein the dosage form releases from 0 to 20% of a compound in 0 to 2 hours, from 20 to 50% of the compound in 2 to 12 hours, from 50 to 85% of the compound in 3 to 20 hours and greater than 75% of the compound in 5 to 18 hours.

9. The dosage form of claim 6, wherein the dosage form comprises an osmotic dosage form, a compound-releasing polymer, a compound-releasing lipid, a compound-releasing wax, tiny timed-release pills, or compound-releasing beads.

10. A method for achieving sustained release of a GABA analog in a patient in need of therapy with the GABA analog, comprising orally administering to the patient a sustained release dosage form containing a therapeutically effective amount of the compound of claim 1.

11. A method for treating epilepsy, depression, anxiety, psychosis, or in a patient, comprising administering to a patient in need of such treatment a therapeutically effective amount of the oral dosage form of claim 6.

* * * * *

UNITED STATES PATENT AND TRADEMARK OFFICE
CERTIFICATE OF CORRECTION

PATENT NO. : 7,420,002 B2  Page 1 of 1
APPLICATION NO. : 10/480293
DATED : September 2, 2008
INVENTOR(S) : Gallop et al.

It is certified that error appears in the above-identified patent and that said Letters Patent is hereby corrected as shown below:

Claim 11, column 64, line 34 should read: -- psychosis, or pain in a patient, comprising administering to a --.

Signed and Sealed this

Twenty-second Day of September, 2009

David J. Kappos
*Director of the United States Patent and Trademark Office*